(12) United States Patent
Cadilla et al.

(10) Patent No.: US 7,439,259 B2
(45) Date of Patent: Oct. 21, 2008

(54) THIAZOLE DERIVATIVES FOR TREATING PPAR RELATED DISORDERS

(75) Inventors: Rodolfo Cadilla, Durham, NC (US); Romain Luc Marie Gosmini, Les Ulis (FR); Millard Hurst Lambert, III, Durham, NC (US); Michael Lawrence Sierra, Les Ulis (FR)

(73) Assignee: SmithKline Beecham Corporation, Philadelphia, PA (US)

( * ) Notice: Subject to any disclaimer, the term of this patent is extended or adjusted under 35 U.S.C. 154(b) by 266 days.

(21) Appl. No.: 11/465,135

(22) Filed: Aug. 17, 2006

(65) Prior Publication Data

US 2006/0276519 A1    Dec. 7, 2006

Related U.S. Application Data

(63) Continuation of application No. 10/451,313, filed on Oct. 20, 2003, now Pat. No. 7,105,551.

(51) Int. Cl.
*A61K 31/421* (2006.01)
*A61K 31/426* (2006.01)
*C07D 263/32* (2006.01)
*C07D 277/24* (2006.01)

(52) U.S. Cl. ........................ 514/365; 514/374
(58) Field of Classification Search ................ None
See application file for complete search history.

(56) References Cited

U.S. PATENT DOCUMENTS

| | | | |
|---|---|---|---|
| 6,518,290 B1 * | 2/2003 | Sierra | 514/365 |
| 6,710,063 B1 | 3/2004 | Chao et al. | |
| 6,723,740 B2 * | 4/2004 | Chao et al. | 514/365 |
| 7,091,225 B2 * | 8/2006 | Sierra | 514/365 |
| 7,105,551 B2 * | 9/2006 | Cadilla et al. | 514/365 |
| 7,153,878 B2 * | 12/2006 | Conner et al. | 514/365 |
| 7,196,107 B2 * | 3/2007 | Beswick et al. | 514/365 |
| 7,351,728 B2 * | 4/2008 | Brooks et al. | 514/374 |

FOREIGN PATENT DOCUMENTS

| | | | |
|---|---|---|---|
| EP | 0612743 | | 9/1997 |
| EP | 0710659 | | 1/2004 |
| WO | WO 01/00603 | * | 1/2001 |
| WO | WO 01/40207 | * | 6/2001 |
| WO | 02/18355 | | 3/2002 |

* cited by examiner

*Primary Examiner*—Fiona T Powers
(74) *Attorney, Agent, or Firm*—Robert H. Brink

(57) ABSTRACT

The present invention provides combinations of compounds of formula (I) and other therapeutic agents for the treatment of PPAR related diseases.

(1)

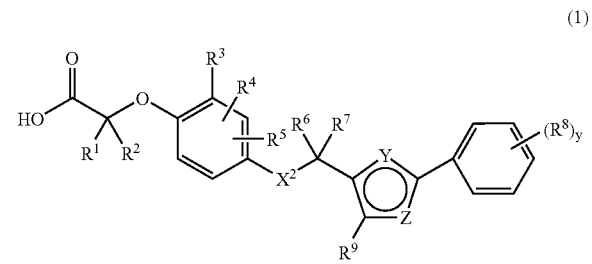

12 Claims, No Drawings

THIAZOLE DERIVATIVES FOR TREATING PPAR RELATED DISORDERS

This application is a continuation of Ser. No. 10/451,313 filed Oct. 20, 2003 now U.S. Pat. No. 7,105,551, which claims priority to GB 0031107.6 filed Dec. 20, 2000. Both applications are incorporated herein by reference in their entirety.

The present invention relates to certain novel compounds. In particular, the present invention relates to compounds that activate human peroxisome proliferator activated receptors ("hPPARs"). The present invention also relates to method for preparing the compounds, their use in medicine, pharmaceutical compositions containing them and methods for the prevention or treatment of PPAR mediated diseases or conditions.

Several independent risk factors have been associated with cardiovascular disease. These include hypertension, increased fibrinogen levels, high levels of triglycerides, elevated LDL cholesterol, elevated total cholesterol, and low levels of HDL cholesterol. HMG CoA reductase inhibitors ("statins") are useful for treating conditions characterized by high LDL-c levels. It has been shown that lowering LDL-c is not sufficient for reducing the risk of cardiovascular disease in some patients, particularly those with normal LDL-c levels. This population pool is identified by the independent risk factor of low HDL-c. The increased risk of cardiovascular disease associated with low HDL-c levels has not yet been successfully addressed by drug therapy (i.e. currently there are no drugs on the market that are useful for raising HDL-c). (Bisgaier, C. L.; Pape, M. E. Curr. Pharm. Des. 1998, 4, 53-70).

Syndrome X (including metabolic syndrome) is loosely defined as a collection of abnormalities including hyperinsulemia, obesity, elevated levels of triglycerides, uric acid, fibrinogen, small dense LDL particles, and plasminogen activator inhibitor 1 (PAI-1), and decreased levels of HDL-c.

NIDDM is described as insulin resistance, which in turn causes anomalous glucose output and a decrease in glucose uptake, by skeletal muscle. These factors eventually lead to impaired glucose tolerance (IGT) and hyperinsulinemia.

Peroxisome Proliferator Activated Receptors (PPARs) are orphan receptors belonging to the steroid/retinoid receptor superfamily of ligand-activated transcription factors. See, for example Willson T. M. and Wahli, W., Curr. Opin. Chem. Biol., 1, pp 235-241 (1997) and Willson T. M. et. al., J. Med. Chem., 43, p 527-549 (2000). The binding of agonist ligands to the receptor results in changes in the expression level of MRNA's enclded by PPAR target genes.

Three mammalian Peroxisome Proliferator-Activated Receptors have been isolated and termed PPAR-alpha, PPAR-gamma, and PPAR-delta (also known as NUC1 or PPAR-beta). These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signalling cascade and lipid homeostasis (H. Keller and W. Wahli, Trends Endocrinol. Metab 291-296, 4 (1993)).

It has now been reported that thiazolidinediones are potent and selective activators of PPAR-gamma and bind directly to the PPAR-gamma receptor (J. M. Lehmann et. al., J. Biol. Chem. 12953-12956, 270 (1995)), providing evidence that PPAR-gamma is a possible target for the therapeutic actions of the thiazolidinediones.

Activators of the nuclear receptor PPARγ, for example troglitazone, have been shown in the clinic to enhance insulin-action, reduce serum glucose and have small but significant effects on reducing serum triglyceride levels in patients with Type 2 diabetes. See, for example, D. E. Kelly et al., Curr. Opin. Endocrinol. Diabetes, 90-96, 5 (2), (1998); M. D. Johnson et al., Ann. Pharmacother., 337-348, 32 (3), (1997); and M. Leutenegger et al., Curr. Ther. Res., 403-416, 58 (7), (1997).

The mechanism for this triglyceride lowering effect appears to be predominantly increased clearance of very low density lipoproteins (VLDL) through induction of lipoprotein lipase (LPL) gene expression. See, for example, B. Staels et al., Arterioscler. Thromb., Vasc. Biol., 1756-1764, 17 (9), (1997).

Fibrates are a class of drugs which may lower serum triglycerides 20-50%, lower LDLc 10-15%, shift the LDL particle size from the more atherogenic small dense to normal dense LDL, and increase HDLc 10-15%. Experimental evidence indicates that the effects of fibrates on serum lipids are mediated through activation of PPARα. See, for example, B. Staels et al., Curr. Pharm. Des., 1-14, 3 (1), (1997). Activation of PPARα results in transcription of enzymes that increase fatty acid catabolism and decrease de-novo fatty acid synthesis in the liver resulting in decreased triglyceride synthesis and VLDL production/secretion. In addition, PPARα activation decreases production of apoC-III. Reduction in apoC-III, an inhibitor of LPL activity, increases clearance of VLDL. See, for example, J. Auwerx et al., Atherosclerosis, (Shannon, Irel.), S29-S37, 124 (Suppl), (1996).

Certain compounds that activate or otherwise interact with one or more of the PPARs have been implicated in the regulation of triglyceride and cholesterol levels in animal models. See, for example, U.S. Pat. Nos. 5,847,008 (Doebber et al.) and 5,859,051 (Adams et al.) and PCT publications WO 97/28149 (Leibowitz et al.) and WO99/04815 (Shimokawa et at.). In a recent report (Berger et al., J. Biol. Chem. 1999), vol. 274, pp. 6718-6725) it was stated that PPARδ activation does not appear to modulate glucose or triglyceride levels.

Accordingly the invention provides a compound of formula 1 and pharmaceutically acceptable salts and solvates and hydrolysable esters thereof.

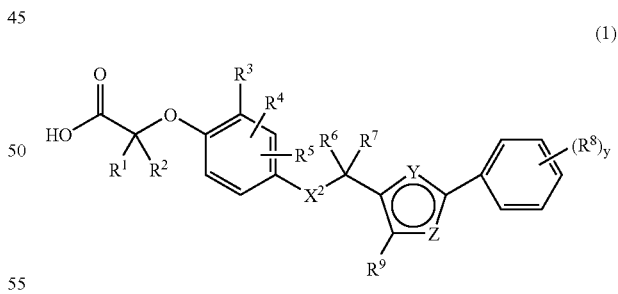

(1)

wherein:

$R^1$ and $R^2$ are independently H or $C_{1-3}$ alkyl, or $R^1$ and $R^2$ may together with the carbon atom to which they are bonded form a 3-6 membered cycloalkyl ring, and at least one of $R^1$ and $R^2$ must be other than H;

$X^2$ is O, S, or $(CR^{10}OR^{11})_n$ where n is 1 or 2 and $R^{10}$ and $R^{11}$ are independently H, fluorine, or $C_{1-6}$alkyl;

$R^3$, $R^4$, and $R^5$ are independently H, $C_{1-3}$alkyl, $OCH_3$, $CF_3$, allyl, or halogen.

one of Y and Z is N, the other is S or O;

R⁶ and R⁷ are independently H, phenyl, benzyl, fluorine, OH, $C_{1-6}$ alkyl, allyl, or R⁶ and R⁷ may together with the carbon atom to which they are bonded form a carbonyl group;

R⁹ is H, $CF_3$, or $C_{1-6}$alkyl;

Each R⁸ is independently $CF_3$, $C_{1-3}$alkyl, $OCH_3$, or halogen;

y is 0, 1, 2, 3, 4, or 5.

In another aspect, the present invention discloses a method for prevention or treatment of a disease or condition mediated by one or more human PPAR alpha, gamma or delta ("hPPARs") comprising administration of a therapeutically effective amount of a compound of this invention. hPPAR mediated diseases or conditions include dyslipidemia including associated diabetic dyslipidemia and mixed dyslipidemia, syndrome X (as defined in this application this embraces metabolic syndrome), heart failure, hypercholesteremia, cardiovascular disease including atherosclerosis, arteriosclerosis, and hypertriglyceridemia, type II diabetes mellitus, type I diabetes, insulin resistance, hyperlipidemia, inflammation, epithelial hyperproliferative diseases including eczema and psoriasis and conditions associated with the lung and gut and regulation of appetite and food intake in subjects suffering from disorders such as obesity, anorexia bulimia, and anorexia nervosa. In particular, the compounds of this invention are useful in the treatment and prevention of diabetes and cardiovascular diseases and conditions including atherosclerosis, arteriosclerosis, hypertriglyceridemia, and mixed dyslipidaemia.

In another aspect, the present invention provides pharmaceutical compositions comprising a compound of the invention, preferably in association with a pharmaceutically acceptable diluent or carrier.

In another aspect, the present invention provides a compound of the invention for use in therapy, and in particular, in human medicine.

In another aspect, the present invention provides the use of a compound of the invention for the manufacture of a medicament for the treatment of a hPPAR mediated disease or condition.

As used herein, "a compound of the invention" means a compound of formula (I) or a pharmaceutically acceptable salt, or solvate, or hydrolysable ester thereof.

While hydrolyzable esters are included in the scope of this invention, the acids are preferred because the data suggests that while the esters are useful compounds, it may actually be the acids to which they hydrolyse that are the active compounds. Esters that hydrolyse readily can produce the carboxylic acid in the assay conditions or in vivo. Generally the carboxylic acid is active in both the binding and transient transfection assays, while the ester does not usually bind well but is active in the transient transfection assay presumably due to hydrolysis. Preferred hydrolysable esters are $C_{1-6}$ alkyl esters wherein the alkyl group may be straight chain or branched chain. Methyl or ethyl esters are more preferred.

Preferably at least one of R¹ and R² is $CH_3$. More preferably R¹ and R² are both $CH_3$;

Preferably X² is O, S, or $C(R^{10}R^{11})$. Most preferably X² is O or S;

Preferably R³ is $CH_3$;

Preferably R⁴ and R⁵ are independently H or methyl;

Preferably Z is N;

Preferably Y is S.

Preferably R¹⁰ and R¹¹ are H;

Preferably R⁹ is $CH_3$.

Preferably R⁶ is H, $CH_3$, $CH_2CH_3$ or allyl. Most preferably R⁶ is H, $CH_3$, or $CH_2CH_3$.

Preferably R⁷ is H.

Preferably each R⁸ is independently F or $CF_3$.

Preferably y is 1 or 2. When y is 2, preferably one of the substituents is halogen and the other is $CF_3$. When y is 1, preferably the substituent is in the para position on the ring.

While the preferred groups for each variable have generally been listed above separately for each variable, preferred compounds of this invention include those in which several or each variable in Formula (I) is selected from the preferred, more preferred, or most preferred groups for each variable. Therefore, this invention is intended to include all combinations of preferred and most preferred groups.

Preferred compounds of formula 1 include:

2-{4-[({2-[2-fluoro-4-(trifluoromethyl)phenyl]-4-methyl-1,3-thiazol-5-yl}methyl)sulfanyl]-2-methylphenoxy}-2-methylpropanoic acid 2-methyl-2-(2-methyl-4-{1-[4-methyl-2-(4-trifluoromethylphenyl)thiazol-5-yl]ethoxy}phenoxy)propionic acid ethyl ester 2-methyl-2-(2-methyl-4-{1-[4-methyl-2-(4-trifluoromethylphenyl)thiazol-5-yl]propoxy}phenoxy)propionic acid ethyl ester 2-methyl-2-(2-methyl-4-{1-[4-methyl-2-(4-trifluoromethylphenyl)thiazol-5-yl]but-3-enyloxy}phenoxy)propionic acid ethyl ester 2-methyl-2-(2-methyl-4-{1-[4-methyl-2-(4-trifluoromethylphenyl)-thiazol-5-yl]phenylmethoxy}phenoxy)propionic acid ethyl ester (2-methyl-4-{1-[4-methyl-2-(4-trifluoromethylphenyl)-thiazol-5-yl]ethoxy}-phenoxy)-acetic acid ethyl ester 2-methyl-2-(2-methyl-4-{1-[4-methyl-2-(3-Fluoro-4-trifluoromethylphenyl)-thiazol-5-yl]ethoxy}-phenoxy)-propionic acid ethyl ester (S)-2-methyl-2-(2-methyl-4-{1-[4-methyl-2-(4-trifluoromethylphenyl)-thiazol-5-yl]ethoxy}-phenoxy)-propionic acid ethyl ester (R)-2-methyl-2-(2-methyl-4-{1-[4-methyl-2-(4-trifluoromethylphenyl)-thiazol-5-yl]ethoxy}-phenoxy)-propionic acid ethyl ester 2-(4-{1-[2-(4-chloro-phenyl)-4-methyl-thiazol-5-yl]-ethoxy}-2-methyl-phenoxy)-2-methyl-propionic acid ethyl ester 2-(4-{1-[2-(3,4-dichloro-phenyl)-4-methyl-thiazol-5-yl]-ethoxy}-2-methyl-phenoxy)-2-methyl-propionic acid ethyl ester 2-(4-{1-[2-(4-ethyl-phenyl)-4-methyl-thiazol-5-yl]-ethoxy}-2-methyl-phenoxy)-2-methyl-propionic acid ethyl ester 2-(4-{1-[2-(2-fluoro-4-trifluoromethyl-phenyl)-4-methyl-thiazol-5-yl]-ethoxy}-2-methyl-phenoxy)-2-methyl-propionic acid ethyl ester 2-methyl-2-(2-methyl-4-{1-[2-(4-trifluoromethyl-phenyl)-thiazol-5-yl]-ethoxy}-phenoxy)-propionic acid ethyl ester 2-methyl-2-(2-methyl-4-{1-methyl-1-[4-methyl-2-(4-trifluoromethyl-phenyl)-thiazol-5-yl]-ethoxy}-phenoxy)-propionic acid ethyl ester 2-methyl-2-(2-methyl-4-{1-methyl-1-[2-(4-trifluoromethyl-phenyl)-thiazol-5-yl]-ethoxy}-phenoxy)-propionic acid ethyl ester (R)-2-methyl-2-(2-methyl-4-{1-[4-methyl-2-(4-trifluoromethyl-phenyl)-thiazol-5-yl]propoxy}-phenoxy)-propionic acid ethyl ester (S)-2-methyl-2-(2-methyl-4-{1-[4-methyl-2-(4-trifluoromethyl-phenyl)-thiazol-5-yl]propoxy}-phenoxy)-propionic acid ethyl ester 2-methyl-2-(2-methyl-4-{1-[4-methyl-2-(4-trifluoromethyl-phenyl)-thiazol-5-yl]butoxy}-phenoxy)-propionic acid ethyl ester 2-methyl-{2-methyl-2-(2-methyl-4-{1-[4-methyl-2-(4-trifluoromethyl-phenyl)-thiazol-5-yl]-propoxy}-henoxy)}-propionic acid ethyl ester 2-methyl-2-(2-methyl-4-{1-[4-methyl-2-(4-trifluoromethyl-phenyl)-thiazol-5-yl]pentyloxy}-phenoxy)-propionic acid ethyl ester 2-(4-{cyclopentyl-[4-methyl-2-(4-trifluoromethyl-phenyl)-thiazol-5-yl]-methoxy}-2-methyl-phenoxy)-2-methyl-propionic acid ethyl ester 2-methyl-2-(2-methyl-4-[4-methyl-2-(4-trifluoromethylphenyl)thiazol-5-yl-methoxy]phenoxy)propionic acid ethyl ester 2-methyl-2-(2-methyl-4-{1-[4-methyl-2-(4-trifluoromethyl-phenyl)-thiazol-5-yl]-2-phenyl-ethoxy}-phenoxy)-propionic acid ethyl ester 2-methyl-2-(2-methyl-4-{1-[4-methyl-2-(4-trifluoromethyl-phenyl)-thiazol-5-yl]-ethylsulfanyl}-phenoxy)-propionic acid ethyl ester 2-methyl-2-(2-methyl-4-{1-[2-(4-trifluoromethyl-phenyl)-thiazol-5-yl]-ethylsulfanyl}-phenoxy)-propionic acid ethyl ester 2-methyl-2-(2-methyl-4-{1-methyl-1-[4-methyl-2-(4-trifluoromethyl-phenyl)-thiazol-5-yl]-ethylsulfanyl}-phenoxy)-propionic acid ethyl ester 2-methyl-2-(2-methyl-4-{1-methyl-1-[2-(4-trifluoromethyl-phenyl)-thiazol-5-yl]-ethylsulfanyl}-phenoxy)-propionic acid ethyl ester 2-methyl-2-(2-methyl-4-{1-[4-methyl-2-(4-trifluoromethyl-phenyl)-thiazol-5-yl]-propylsulfanyl}-phenoxy)-propionic acid ethyl ester 2-methyl-2-(2-methyl-4-{1-[4-methyl-2-(4-trifluoromethylphenyl)-thiazol-5-yl]phenylmethoxy}phenoxy)propionic acid 2-methyl-2-(2-methyl-4-{1-[4-methyl-2-(4-trifluoromethylphenyl)thiazol-5-yl]ethoxy}phenoxy)propionic acid 2-methyl-2-(2-methyl-4-{1-[4-methyl-2-(4-trifluoromethylphenyl)thiazol-5-yl]propoxy}phenoxy)propionic acid 2-methyl-2-(2-methyl-4-{1-[4-methyl-2-(4-trifluoromethylphenyl)-thiazol-5-yl]but-3-enyloxy}phenoxy)propionic acid (2-methyl-4-{1-[4-methyl-2-(4-trifluoromethylphenyl)-thiazol-5-yl]ethoxy}-phenoxy)-acetic acid 2-methyl-2-(2-methyl-4-{1-[4-methyl-2-(3-Fluoro-4-trifluoromethylphenyl)-thiazol-5-yl]ethoxy}-phenoxy)-propionic acid (S)-2-methyl-2-(2-methyl-4-{1-[4-methyl-2-(4-trifluoromethylphenyl)-thiazol-6-yl]ethoxy}-phenoxy)-propionic acid (R)-2-methyl-2-(2-methyl-4-{1-[4-methyl-2-(4-trifluoromethylphenyl)-thiazol-5-yl]ethoxy}-phenoxy)-propionic acid 2-(4-{1-[2-(4-chloro-phenyl)-4-methyl-thiazol-5-yl]-ethoxy}-2-methyl-phenoxy)-2-methyl-propionic acid 2-(4-{1-[2-(3,4-dichloro-phenyl)-4-methyl-thiazol-5-yl]-ethoxy}-2-methyl-phenoxy)-2-methyl-propionic acid 2-(4-{1-[2-(4-ethyl-phenyl)-4-methyl-thiazol-5-yl]-ethoxy}-2-methyl-phenoxy)-2-methyl-propionic acid 2-(4-{1-[2-(2-fluoro-4-trifluoromethyl-phenyl)-4-methyl-thiazol-5-yl]-ethoxy}-2-methyl-phenoxy)-2-methyl-propionic acid 2-methyl-2-(2-methyl-4-{1-[2-(4-trifluoromethyl-phenyl)-thiazol-5-yl]-ethoxy}-phenoxy)-propionic acid 2-methyl-2-(2-methyl-4-{1-methyl-1-[4-methyl-2-(4-trifluoromethyl-phenyl)-thiazol-5-yl]-ethoxy}-phenoxy)-propionic acid 2-methyl-2-(2-methyl-4-{1-methyl-1-[2-(4-trifluoromethyl-phenyl)-thiazol-5-yl]-ethoxy}-phenoxy)-propionic acid (R)-2-methyl-2-(2-methyl-4-{1-[4-methyl-2-(4-trifluoromethyl-phenyl)-thiazol-5-yl]propoxy}-phenoxy)-propionic acid (S)-2-methyl-2-(2-methyl-4-{1-[4-methyl-2-(4-trifluoromethyl-phenyl)-thiazol-5-yl]propoxy}-phenoxy)-propionic acid 2-methyl-2-(2-methyl-4-{1-[4-methyl-2-(4-trifluoromethyl-phenyl)-thiazol-5-yl]butoxy}-phenoxy)-propionic acid 2-methyl-{2-methyl-2-(2-methyl-4-{1-[4-methyl-2-(4-trifluoromethyl-phenyl)-thiazol-5-yl]-propoxy}-henoxy)}-propionic acid 2-methyl-2-(2-methyl-4-{1-[4-methyl-2-(4-trifluoromethyl-phenyl)-thiazol-5-yl]pentyloxy}-phenoxy)-propionic acid 2-(4-{cyclopentyl-[4-methyl-2-(4-trifluoromethyl-phenyl)-thiazol-5-yl]-methoxy}-2-methyl-phenoxy)-2-methyl-propionic acid 2-methyl-2-(2-methyl-4-[4-methyl-2-(4-trifluoromethylphenyl)thiazol-5-yl-methoxy]phenoxy)propionic acid 2-methyl-2-(2-methyl-4-{1-[4-methyl-2-(4-trifluoromethyl-phenyl)-thiazol-5-yl]-2-phenyl-ethoxy}-phenoxy)-propionic acid 2-methyl-2-(2-methyl-4-{1-[4-methyl-2-(4-trifluoromethyl-phenyl)-thiazol-5-yl]-ethylsulfanyl}-phenoxy)-propionic acid 2-methyl-2-(2-methyl-4-{1-[2-(4-trifluoromethyl-phenyl)-thiazol-5-yl]-ethylsulfanyl}-phenoxy)-propionic acid 2-methyl-2-(2-methyl-4-{1-methyl-1-[4-methyl-2-(4-trifluoromethyl-phenyl)-thiazol-5-yl]-ethylsulfanyl}-phenoxy)-propionic acid 2-methyl-2-(2-methyl-4-{1-methyl-1-[2-(4-trifluoromethyl-phenyl)-thiazol-5-yl]-ethylsulfanyl}-phenoxy)-propionic acid 2-methyl-2-(2-methyl-4-{1-[4-methyl-2-(4-trifluoromethyl-phenyl)-thiazol-5-yl]-propylsulfanyl}-phenoxy)-propionic acid Most preferred compounds of formula 1 include:

2-{4-[({2-[2-fluoro-4-(trifluoromethyl)phenyl]-4-methyl-1,3-thiazol-5-yl}methyl)sulfanyl]-2-methylphenoxy}-2-methylpropanoic acid (S)-2-methyl-2-(2-methyl-4-{1-[4-methyl-2-(4-trifluoromethylphenyl)-thiazol-5-yl]ethoxy}-phenoxy)-propionic acid (R)-2-methyl-2-(2-methyl-4-{1-[4-methyl-2-(4-trifluoromethylphenyl)-thiazol-5-yl]ethoxy}-phenoxy)-propionic acid (R)-2-methyl-2-(2-methyl-4-{1-[4-methyl-2-(4-trifluoromethyl-phenyl)-thiazol-5-yl]propoxy}-phenoxy)-propionic acid (S)-2-methyl-2-(2-methyl-4-{1-[4-methyl-2-(4-trifluoromethyl-phenyl)-thiazol-5-yl]propoxy}-phenoxy)-propionic acid Those skilled in the art will recognize that stereocenters exist in compounds of formula (I). Accordingly, the present invention includes all possible stereoisomers and geometric isomers of formula (I) and includes not only racemic compounds but this invention is also intended to cover each of these isomers in their racemic, enriched, or purified forms.

When a compound of formula (I) is desired as a single enantiomer, it may be obtained either by resolution of the final product or by stereospecific synthesis using an optically active catalyst or a catalytic system with optically active ligands or isomerically pure starting material or any convenient intermediate. Resolution of the final product, an intermediate or a starting material may be effected by any suitable method known in the art. See, for example, Stereochemistry of Carbon Compounds by E. L. Eliel (Mcgraw Hill, 1962) and Tables of Resolving Agents by S. H. Wilen. Additionally, in situations where tautomers of the compounds of formula (I) are possible, the present invention is intended to include all tautomeric forms of the compounds. In particular, in many of the preferred compounds of this invention the carbon atom to which $R^6$ and $R^7$ are bonded is chiral. In some of these chiral compounds the activities at the various PPAR receptors varies between the S and R isomers. Which of these isomers is preferred depends on the particular desired utility of the compound. In other words, even with the same compound, it is possible that the S isomer will be preferred for some uses, while the R isomer will be preferred for others.

The hPPAR agonists of formula (I) may be agonists of only one type ("selective agonists"), agonists for two PPAR subtypes ("dual agonists"), or agonists for all three subtypes ("pan agonists"). As used herein, by "agonist", or "activating compound", or "activator", or the like, is meant those compounds which have a pKi of at least 6.0 preferably at least 7.0 to the relevant PPAR, for example hPPARδ, in the binding assay described below, and which achieve at least 50% activation of the relevant PPAR relative to the appropriate indicated positive control in the transfection assay described below at concentrations of $10^{-5}$ M or less. More preferably, the agonists of this invention achieve 50% activation of at least one human PPAR in the relevant transfection assay at concentrations of $10^{-6}$ M or less. Preferably, the compounds of formula (I) are hPPAR agonists. More preferably the compounds are hPPARδ agonists. Most preferably they are dual agonists of hPPARδ and hPPARα, or pan agonists.

It will also be appreciated by those skilled in the art that the compounds of the present invention may also be utilised in the form of a pharmaceutically acceptable salt or solvate thereof. The physiologically acceptable salts of the compounds of formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, palmoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, N,N'-dibenzylethylenediamine, chloroprocaine, choline, diethanolamine, ethylenediamine, N-methylglucamine and procaine salts. Those skilled in the art of organic chemistry will appreciate that many organic compounds can form complexes with solvents in which they are reacted or from which they are precipitated or crystallized. These complexes are known as "solvents". For example, a complex with water is known as a "hydrate".

Solvates of the compound of formula (I) are within the scope of the invention. References hereinafter to a compound according to the invention include both compounds of formula (I) and their pharmaceutically acceptable salts and solvates.

The compounds of the invention and their pharmaceutically acceptable derivatives are conveniently administered in the form of pharmaceutical compositions. Such compositions may conveniently be presented for use in conventional manner in admixture with one or more physiologically acceptable carriers or excipients.

While it is possible that compounds of the present invention may be therapeutically administered as the raw chemical, it is preferable to present the active ingredient as a pharmaceutical formulation. The carrier(s) must be "acceptable" in the sense of being compatible with the other ingredients of the formulation and not deleterious to the recipient thereof.

Accordingly, the present invention further provides for a pharmaceutical formulation comprising a compound of formula (I) or a pharmaceutically acceptable salt or solvate thereof together with one or more pharmaceutically acceptable carriers therefore and, optionally, other therapeutic and/or prophylactic ingredients.

The formulations include those suitable for oral, parenteral (including subcutaneous e.g. by injection or by depot tablet, intradermal, intrathecal, intramuscular e.g. by depot and intravenous), rectal and topical (including dermal, buccal and sublingual) administration although the most suitable route may depend upon for example the condition and disorder of the recipient. The formulations may conveniently be presented in unit dosage form and may be prepared by any of the methods well known in the art of pharmacy. All methods include the step of bringing into association the compounds ("active ingredient") with the carrier, which constitutes one or more accessory ingredients. In general the formulations are prepared by uniformly and intimately bringing into association the active ingredient with liquid carriers or finely divided solid carriers or both and then, if necessary, shaping the product into the desired formulation.

Formulations suitable for oral administration may be presented as discrete units such as capsules, cachets or tablets (e.g. chewable tablets in particular for paediatric administration) each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a other conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulfate. Moulded tablets may be made by moulding in a suitable machine a mixture of the powdered compound moistened with an inert liquid diluent. The tablets may optionally be coated or scored and may be formulated so as to provide slow or controlled release of the active ingredient therein. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of a sterile liquid carrier, for example, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter, hard fat or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

The compounds may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

In addition to the ingredients particularly mentioned above, the formulations may include other agents conventional in the art having regard to the type of formulation in question, for example those suitable for oral administration may include flavouring agents.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02-5000 mg per day, preferably 1-1500 mg per day. The desired dose may conveniently be presented in a single dose or as divided doses administered at appropriate intervals, for example as two, three, four or more sub-doses per day. The formulations according to the invention may contain between 0.1-99% of the active ingredient, conveniently from 30-95% for tablets and capsules and 3-50% for liquid preparations.

The compound of formula (I) for use in the instant invention may be used in combination with other therapeutic agents for example, statins and/or other lipid lowering drugs for example MTP inhibitors and LDLR upregulators. The compounds of the invention may also be used in combination with antidiabetic agents, e.g. metformin, sulfonylureas and/or PPAR gamma, PPAR alpha or PPAR alpha/gamma agonists (for example thiazolidinediones such as e.g. Pioglitazone and Rosiglitazone). The compounds may also be used in combination with antihypertensive agents such as angistensin antagonists e.g. telmisartan, calcium channel antagonists e.g. lacidipine and ACE inhibitors e.g. enalapril. The invention thus provides in a further aspect the use of a combination comprising a compound of formula (I) with a further therapeutic agent in the treatment of a hPPAR mediated disease.

When the compounds of formula (I) are used in combination with other therapeutic agents, the compounds may be administered either sequentially or simultaneously by any convenient route.

The combinations referred to above may conveniently be presented for use in the form of a pharmaceutical formulation and thus pharmaceutical formulations comprising a combination as defined above optimally together with a pharmaceutically acceptable carrier or excipient comprise a further aspect of the invention. The individual components of such combinations may be administered either sequentially or simultaneously in separate or combined pharmaceutical formulations.

When combined in the same formulation it will be appreciated that the two compounds must be stable and compatible with each other and the other components of the formulation and may be formulated for administration. When formulated separately they may be provided in any convenient formulation, conveniently in such a manner as are known for such compounds in the art.

When a compound of formula (I) is used in combination with a second therapeutic agent active against the same hPPAR mediated disease, the dose of each compound may differ from that when the compound is used alone. Appropriate doses will be readily appreciated by those skilled in the art.

Compounds of this invention may be conveniently prepared by a general process wherein a moiety like A is coupled to an alcohol (B and D) using the Mitsunobu protocol (O. Mitsunobu, 1981 Synthesis, p 1) or by alkylation of A using a suitable non nucleophilic base such as $K_2CO_3$, $Cs_2CO_3$ or NaH, with an alkyl halide (C, E and F). Note that this synthesis is preferably carried out with the acid group protected by R. Preferably, R is 1-6 alkyl which can be hydrolysed to give an acid of Formula (I), or if readily hydrolyzable, the resulting ester can be administered.

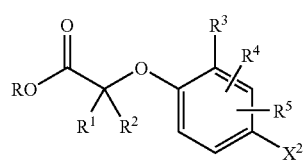

A

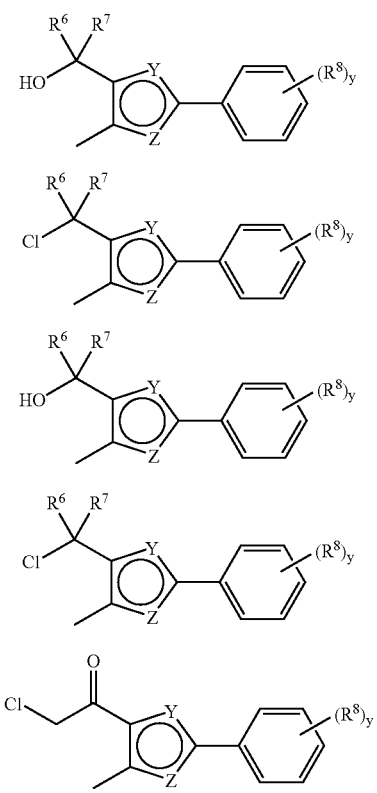

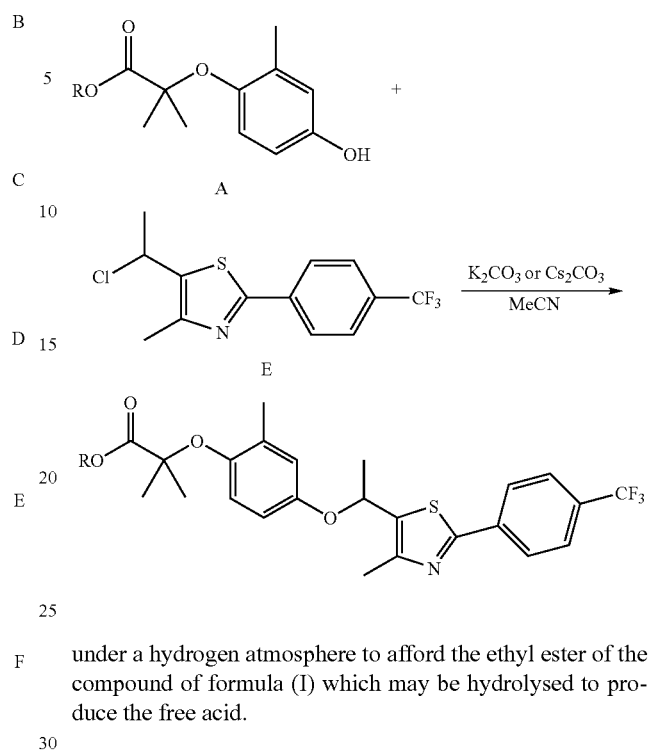

Some of the intermediates of type (A) are commercially available while others can be synthesised as outlined below. The synthesis of intermediates of type (B-F) are also illustrated below.

For example Y is S, Z is N, $R^1$, $R^2$, $R^3$ and $R^6$ are $CH_3$, $R^7$ is H, $X^2$ is O and $R^8$ is para-$CF_3$:

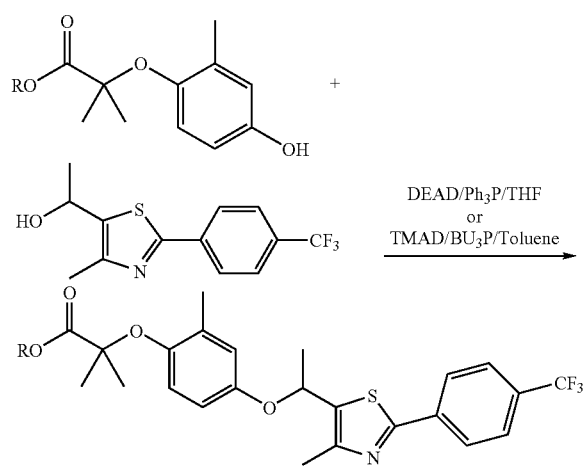

Compounds of the invention may be made by an alternative method in which compounds of formula (G) are reacted with the phosphonium salts of formula (H) under standard Wittig conditions to afford the alkene of formula (J) which can be reduced with Pd/C under a hydrogen atmosphere to afford the ethyl ester of the compound of formula (I) which may be hydrolysed to produce the free acid.

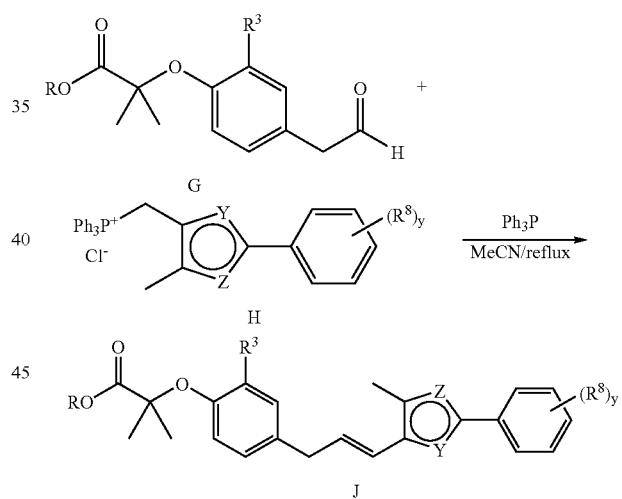

Compounds of formula (H) may be prepared from the reaction between compounds of formula (C) and $PPh_3$ in $CH_3CN$ at reflux for 1 h.

The following illustrates Intermediates and Examples of Formula 1 which should not be construed as constituting a limitation thereto.

The structures of the compounds were confirmed either by nuclear magnetic resonance (NMR) or mass spectrometry (MS). 1H NMR spectra were recorded on a Brucker 300 MHz spectrometer at ambient temperature. NMR shifts (δ) are given in parts per million (ppm), "mp" is melting point and is given in ° C. Column chromatography was carried out using the technique described by W. C. Still et al, J. Org. Chem. 1978, 43, 2923-2925 on Merck silica gel 60 (40-63 μM).

Compounds used as starting materials are either commercially available compounds or known compounds.

Abbreviations
tlc: thin layer chromatography
e.e.: enantiomeric excess
DMSO-$d_6$: deutorated dimethylsulfoxide
$CDCl_3$: deutorated chloroform
$CD_3OD$: deutorated methanol
$C_6H_{12}$: cyclohexane
DCC: dicyohexylcarbodiimide
DMAP: 4-dimethylaminopyridine
DMF: N,N-dimethylformamide
$Et_2O$: diethylether
EtOAc: Ethylacetate
MeOH: Methanol
PBu3: Tributylphosphine
PCC: Pyridinium chlorochromate
Rf: retention fraction
Rt: retention time
TMAD: Azodicarboxylic acid bis[dimethylamide]
THF: tetrahydrofuran
min: minutes
br: broad
s: singlet
d: doublet
dd: doublet of doublet
t: triplet
q: quartet
m: multiplet Intermediate 1:

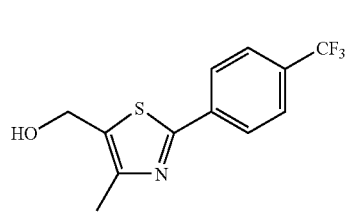

To a well stirred solution of $LiAlH_4$ (1.52 g, 40 mmol) in dry THF (50 mL) at 0° C., was slowly added a solution of ethyl 4-methyl-2-[4-(trifluoromethyl)-phenyl]-thiazole-5-carboxylate (12.6 g, 40 mmol) in dry THF (50 mL). The mixture was stirred at room temperature for 2 h. The reaction was quenched by slow addition at 0° C. of water (2 mL), 5N NaOH (2 mL) and water (6 mL). The precipitate was filtered, washed with EtOAc, MeOH, $CH_2Cl_2$ and THF. After evaporation, a yellow solid was obtained, that was crystallised from MeOH-water to afford intermediate 1 depicted above (9.90 g, 36 mmol, 90%) as a yellow solid mp 120-122° C.

Intermediate 2:

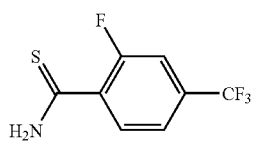

To a solution of 2-fluoro4-(trifluoromethyl)benzonitrile (5.2 g, 27.5 mmol) in 50 mL methanol was added 10 ml of water (137.5 mmol) followed by $NaSH.H_2O$ (7.7 g, 137.5 mmol). After heating at 50° C. for 12 hours, the solvent was removed in vacuo and the residue treated with water (200 mL) and extracted with EtOAc (2×150 mL). The organic layers were dried ($MgSO_4$) and the solvent evaporated to give crude residue which was purified on a Biotage FlashElute with a 40M silica cartridge, eluting with hexane/ethyl acetate (4:1) to yield the title compound as a yellow solid (3.27 g, 53%).

MS $C_8H_6F_4NS$: m/z 224 (M+1); HPLC RT 2.013 (C18 4.6×60 mm, 1% MeOH/0-90% $CH_3CN/H_2O$ (0.1% TFA)/(50 mM TEA/TFA), 4 min @ 3 mL/min @ 254/220 nm).

Intermediate 3:

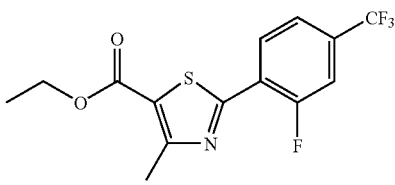

Intermediate 2 was treated with ethyl 2-chloro-3-oxobutanoate in refluxing ethanol overnight and evaporated. The residue was passed through a plug of silica gel with hexane:ethyl acetate (4:1) to afford the title compound as a light yellow solid after evaporation (71%).

MS $C_{14}H_{12}F_4NO_2S$: m/z 333 (M+1)

Intermediate 4:

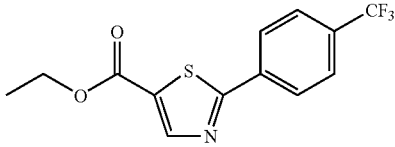

To a solution of NaOEt (9.94 g, 14.6 mmol) in EtOH (50 mL), under a nitrogen atmosphere, were added Ethyl formate (11.81 mL, 14.6 mmol) and chloro acetic acid ethyl ester (10.96 mL, 14.6 mmol) in solution in 50 mL of dry $Et_2O$. The mixture was stirred at rt for 20 hours and filtered after addition of 50 mL of dry $Et_2O$. The resulting solid was dissolved in 100 mL EtOH and after addition of 4-trifluoro methyl thiobenzamide (3 g, 14.6 mmol) stirring to reflux was accomplished for 20 hours. EtOH was removed under reduced pressure and 250 mL of $CH_2Cl_2$ and 50 mL of water were added. The organic layer was separated and dried over $Na_2SO_4$, filtered, concentrated to dryness and purified by flash chromatography $C_6H_{12}$/EtOAc (80:20) to afford the title compound (750 mg, 2.49 mmol) as a white powder in a 17% yield.

GC/MS $C_{13}H_{10}F_3NO_2S$: m/z 301

Intermediate 5:

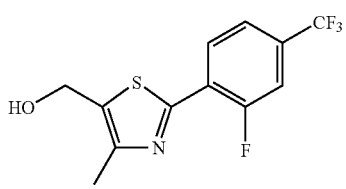

Intermediate 3 was reacted as described in a general LiAlH₄ reduction procedure to afford the title compound as a light yellow solid (83%)

MS C₁₂H₉F₄NOS: m/z 291 (M+1)

Intermediate 6:

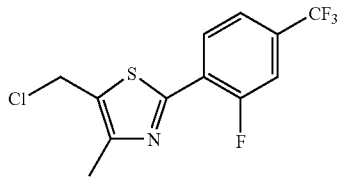

Intermediate 5 was reacted with mesylchloride to afford the title compound as a light yellow solid (100%).

Rf of starting alcohol in 3:1 hexanes/ethyl acetate 0.25
Rf of chloride in 3:1 hexanes/ethyl acetate 0.75

Intermediate 7:

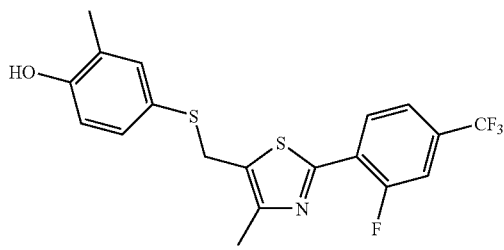

Intermediate 6 was treated with 2-methyl-4-sulfanylphenol as described in a general alkylation procedure to afford the title compound as a yellow oil (0.242 g, 49%).

¹H NMR (CDCl₃); δ 2.22 (s, 3H), 2.25 (s, 3H), 4.15 (s, 2H), 6.69 (d, 1H), 7.13 (d, 1H), 7.20 (s, 1H), 7.50 (m, 2H), 8.39 (t, 1H),

MS C₁₉H₁₆F₄NOS₂: m/z 414 (M+1).

Intermediate 8:

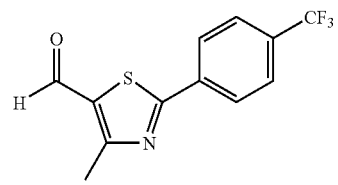

To a solution of Intermediate 1 (75.5 g, 0.276 mmol, 1 eq) in CH₂Cl₂ was added pyridinium chlorochromate (119 g, 0.552 mmol, 2 eq). Then the resulting mixture was stirred at room temperature for 3 hours. The mixture was decanted one night and then filtered over celite and evaporated off. The residue was purified by flash chromatography using CH₂Cl₂ as eluent to give the title compound as a yellow solid (46 g, 0.17 mmol) in a 61.5% yield.

GC/MS: C₁₂H₈F₃NOS: m/z 271

Intermediate 9:

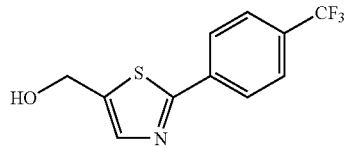

To a solution of intermediate 4 (0.8 g, 2.65 mmol) was added dropwise LiAlH₄ (2.7 mL/1N in THF, 2.7 mmol). The resulting mixture was stirred 30 min at rt and the reaction was quenched by the cautious addition of NH₄Cl and water. The precipitate was filtered, the filtrate was concentrated under vacuo and the residue obtained was flash chromatographed CH₂Cl₂/MeOH (99:1) to afford the title compound (500 mg, 1.93 mmol) as a white solid in a 73% yield.

¹H NMR (CDCl₃) δ: 3.48 (br t, 1H), 4.73 (br d, 2H), 7.52 (m, 3H), 7.82 (d, 2H)

Intermediate 10:

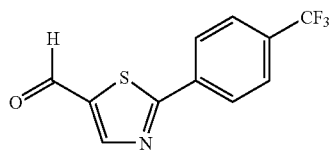

To a solution of intermediate 9 (500 mg, 1.93 mmol) in CH₂Cl₂ (20 mL) was added PCC (830 mg, 2 eq.). After stirring for 2 hours at rt the solvent was evaporated off and the residue flash chromatographed with CH₂Cl₂ to give the title compound (460 mg, 1.78 mmol) as a white powder in a 93% yield.

¹H NMR (CDCl₃) δ: 7.68 (d, 2H), 8.07 (d, 2H), 8.41 (s, 1H), 10.01 (s, 1H)

Intermediate 11:

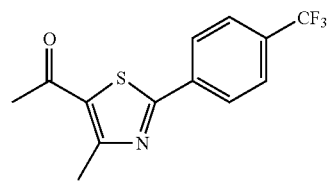

A solution of 4-trifluoromethyl-thiobenzamide (5 g, 24.3 mmol) and 3-chloro-pentane-2,4-dione (3.2 mL, 24.3 mmoles) in 50 mL of EtOH was heated to reflux during 18 hours and evaporated to dryness. The residue was diluted with 250 mL of CH₂Cl₂ and washed with 50 mL of saturated solution of NaHCO₃. The organic phase was separated and dried over Na₂SO₄. After filtration and concentration under vacuo the residue was purified by flash chromatography (CH₂Cl₂) to give the title compound as a tan powder (6.3 g, 22 mmol) in a 90% yield.

GC/MS C₁₃H₁₀F₃NOS: m/z 285

Intermediate 12:

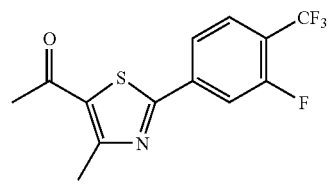

A solution of 3-fluoro-4-trifluoromethyl-thiobenzamide (540 mg, 2.42 mmol) and 3-chloro-pentane-2,4-dione (577 μL, 4.9 mmoles) in 50 mL of EtOH was heated to reflux during 48 hours and evaporated to dryness. The residue was diluted with 250 mL of CH$_2$Cl$_2$ and washed with 50 mL of a saturated solution of NaHCO$_3$. The organic phase was separated and dried over Na$_2$SO$_4$. After filtration and concentration under vacuo the residue was purified by flash chromatography (CH$_2$Cl$_2$) to give the title compound as a tan powder (500 mg, 1.65 mmol) in a 68% yield.

GC/MS C$_{13}$H$_9$F$_4$NOS: m/z 303

Intermediate 13:

A solution of 4-ethyl-thiobenzamide (2 g, 12 mmol) and 3-chloro-pentane-2,4-dione (2.2 mL, 14 mmol) in 30 mL of EtOH was heated to reflux during 18 hours and evaporated to dryness. The residue was diluted with 250 mL of CH$_2$Cl$_2$ and washed with 50 mL of a saturated solution of NaHCO$_3$. The organic phase was separated, dried over Na$_2$SO$_4$, filtered and concentrated under vacuo to give the title compound (2.94 g, 12 mmol) in a quantitative crude yield.

$^1$H NMR (CDCl$_3$) δ: 1.15 (t, 3H), 2.52 (s, 3H), 2.61(q, 2H), 2.72(s, 3H), 7.20 (d, 2H), 7.85(d, 2H)

Intermediate 14:

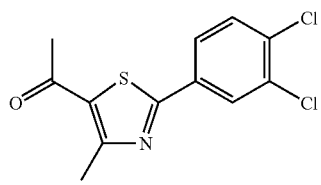

A solution of 3,4-dichloro-thiobenzamide (1.5 g, 7.3 mmol) and 3-chloro-pentane-2,4-dione (1.2 mL, 11 mmol) in 30 mL of EtOH was heated to reflux during 18 hours and evaporated to dryness. The residue was diluted with 250 mL of CH$_2$Cl$_2$ and washed with 50 mL of saturated solution of NaHCO$_3$. The organic phase was separated, dried over Na$_2$SO$_4$, filtered and concentrated under vacuo to give the title compound as an off white powder (1.5 g, 5.2 mmol) in a 71% yield after trituration of the residue in water and washing with pentane.

$^1$H NMR (CDCl$_3$) δ: 2.52 (s, 3H), 2.72(s, 3H), 7.47 (d, 1H), 7.74 (dd, 1H), 8.04 (d, 1H)

Intermediate 15:

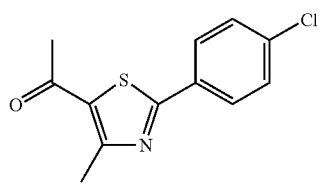

A solution of 4-chloro-thiobenzamide (5 g, 29 mmol) and 3-chloro-pentane-2,4-dione (3.2 mL, 27 mmol) in 50 mL of EtOH was heated to reflux during 5 hours and evaporated to dryness. The residue was diluted with 250 mL of CH$_2$Cl$_2$ and washed with 50 mL of saturated solution of NaHCO$_3$. The organic phase was separated and dried over Na$_2$SO$_4$. After filtration and concentration under vacuo the residue was purified by flash chromatography (CH$_2$Cl$_2$) to give the title compound as (7.2 g, 28.5 mmol) in a quantitative yield.

$^1$H NMR (CDCl$_3$) δ: 2.54 (s, 3H), 2.83 (s, 3H), 7.41 (d, 2H), 8.01 (d, 2H)

Intermediate 16:

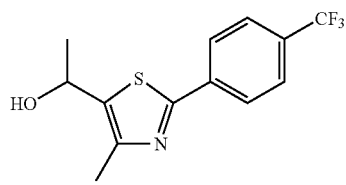

To a solution of intermediate 8 (1.9 g, 7 mmol) in 25 mL of THF was added slowly at −10° C., a solution of 1.4M methylmagnesium bromide in tetrahydrofuran (7 mL, 11.9 mmol, 1.4 eq). The mixture was naturally warmed at room temperature and then stirred for 1.5 hour. The resulting mixture was quenched with saturated NH$_4$Cl solution (100 mL) and extracted with Ethyl Acetate (2×250 mL). The organic phase was washed with brine and water, and then dried over Na$_2$SO$_4$ and evaporated off to give the title compound as a yellow solid (1.9 g, 6.96 mmol) in a 99% crude yield.

GC/MS C$_{13}$H$_{12}$F$_3$NOS: m/z 287 mp: 147° C.

Intermediate 17:

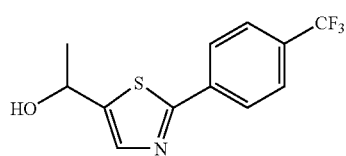

To a solution of the intermediate 10 (1.35 g, 5.25 mmol) was added slowly at −10° C., a solution of 1.4M methylmagnesium bromide in tetrahydrofuran (4.1 ml, 5.8 mmol, 1.1 eq). The mixture was naturally warmed at room temperature and then stirred for 1.5 hour. The resulting mixture was quenched with saturated NH$_4$Cl solution (100 ml) and extracted with Ethyl Acetate(2×250 ml). The organic phase was washed with brine and water, and then dried over Na$_2$SO$_4$ and evaporated off to give the title compound as an off white solid (700 mg, 2.58 mmol) in a 49% yield after purification by flash chromatography CH$_2$Cl$_2$/MeOH (99:1).

GC/MS: C$_{12}$H$_{10}$F$_3$NOS m/z=273

Intermediate 18:

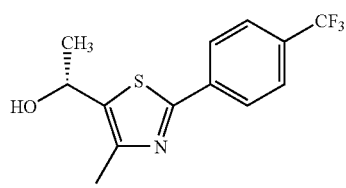

To a solution of intermediate 11 (5 g, 17.5 mmol) and (S)-2-methyl-CBS-oxazaborolidine (3.5 mL, 3.5 mmol, 1N solution in toluene) in anhydrous THF was added slowly at 0° C., a solution of borane-methylsulfide complex (10.5 mL, 21 mmol, 2M solution in THF). The solution was stirred 2.5 hours and a tlc monitoring of an hydrolyzed aliquot indicated that the reaction was completed. 20 mL of MeOH and 100 mL of 0.5 N HCl were added to the solution to quench the reaction. EtOAC extraction (3×200 mL) and acidic washing with diluted HCl (3×50 mL) afforded after drying over $Na_2SO_4$, filtration and concentration under vacuo, 5 g of a white solid. Recrystallization in Hexane/EtOH (200 mL/6 mL) gave after filtration 1.12 g of a racemic powder. The filtrate was evaporated to dryness and the resulting yellow solid was triturated with 100 mL of hexane to yield 3.5 g of a white solid after filtration with an ee=95.5%.

$^1$H NMR(CDCl$_3$, 300Mhz) δ: 1.4(d, 3H), 2.26 (s, 3H), 5.03 (q, 1H), 7.06 (s, 1H), 7.46 (d, 2H), 7.8 (d, 2H)

HPLC Chiralpak AD-RH (4.6×150 mm, 65% CH$_3$CN/ 35% H$_2$O, 0.3 mL/min)

Rt: 17.0 min $[α]^{25}_D$=+38.1 (c=0.25/CHCl$_3$) for ee=95.5%

Intermediate 19:

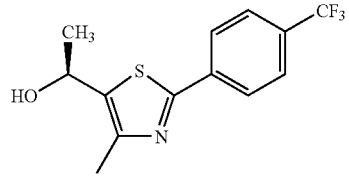

The same experimental procedure as for intermediate 18 was applied to a 3 g quantity of the methylketone using the (R)-2-Methyl-CBS-oxazaborolidine. The title compound (1.7 g; 5.9 mmol) was obtained as a white powder in a 56% yield and with an enantiomeric excess of 79.4% as determined by HPLC. To increase the enantiomeric excess, the resulting alcohol (1.7 g, 5.9 mmol) was coupled with the (R)-(−)-α Methoxyphenylacetic acid (1.1 g; 6.5 mmol) with DCC (1.5 g) and a catalytic amount of DMAP. The two diatereomeric esters had ΔRf=0.1 which allowed the isolation of the less polar fraction, the major one (2.35 g, 5.4 mmol) after flash chromatography using Petroleum Ether/EtOAc (85:15). Finally this ester in solution in 50 mL of EtOH was saponified at 0° C. using 1N NaOH (5.7 mL, 5.7 mmol). After completion the reaction was quenched by dropwise addition at 0° C. of 1N HCl (5.7 mL). After removing EtOH under reduced pressure, extraction with Et$_2$O (200 mL) washing of the organic phase with 25 mL of saturated NaHCO$_3$ afforded the title compound (1.4 g, 4.8 mmol) in 86% yield as a pale oil with an e.e.=98%.

$^1$H NMR(CDCl$_3$, 300 Mhz) δ: 1.60 (d, 3H), 2.44 (s, 3H), 5.21 (q, 1H), 7.66 (d, 2H), 8.0 (d, 2H)

HPLC Chiralpak AD-RH (4.6×150 mm, 65% CH$_3$CN/ 35% H$_2$O, 0.3 mL/min)

Rt: 15.54 min $[α]^{25}_D$=−31 (c=0.32/CHCl$_3$) for ee=86%

Intermediate 20:

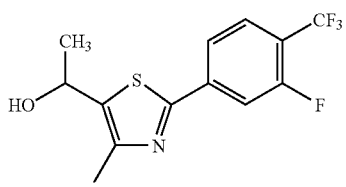

To a solution of intermediate 12 (500 mg, 1.65 mmol) in MeOH (25 mL) was added at once NaBH$_4$ (69 mg, 1.7 mmol). The solution was stirred 30 min and concentrated to dryness. Hydrolysis with 1N HCl (5 mL), followed by Et$_2$O extraction (2×75 mL), drying of the organic phase over Na$_2$SO$_4$, filtration and concentration under vacuo gave a residue which was flash chromatographed CH$_2$Cl$_2$/MeOH (99:1) to afford 380 mg of the title compound.

$^1$H NMR(CDCl$_3$) δ: 1.53 (d, 3H), 2.39 (s, 3H) 5.12 (q, 1H), 7.15 (s, 1H), 7.57 (m, 1H), 7.68 (m, 2H)

Intermediate 21:

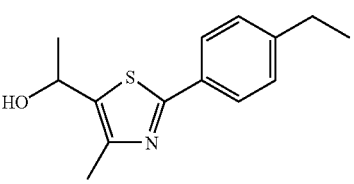

To a solution of methylketone intermediate 13 (3.5 g, 14.2 mmol) in EtOH (50 mL) was added at once NaBH$_4$ (1.1 g, 25 mmol, 2 eq.) at 0° C. After stirring 3 hours at room temperature EtOH was removed under reduced pressure and 1N HCl was added. The resulting precipitate was filtered off, washed with water and dried under vacuum to afford the title compound (1.9 g, 7.6 mmol) in a 54% yield as a white solid.

$^1$H NMR (CDCl$_3$) δ: 1.22 (t, 3H), 1.54(d, 3H), 2.37 (s, 3H), 2.64(q, 2H), 5.14(q, 1H), 7.20 (d, 2H), 7.76(d, 2H)

Intermediate 22:

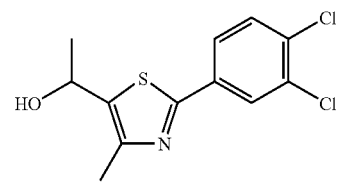

To a solution of methylketone intermediate 14 (1.7 g, 5.9 mmol) in EtOH (25 mL) was added at once NaBH$_4$ (450 mg, 12 mmol, 2 eq.) at 0° C. After stirring 3 hours at room temperature EtOH was removed under reduced pressure and 1N HCl was added. The resulting precipitate was filtered off, washed with water and dried under vacuum to afford the title compound (1.58 g, 5.48 mmol) in a 92% yield as a white solid.

$^1$H NMR (CDCl$_3$) δ: 1.50(d, 3H), 2.01(d, 1H), 2.35 (s, 3H), 5.12(m, 1H), 7.37 (d, 1H, J=8.48 Hz), 7.60(dd, 1H, J=8.3 Hz and 2.07 Hz), 7.92(d, 1H, J=2.1 Hz)

Intermediate 23:

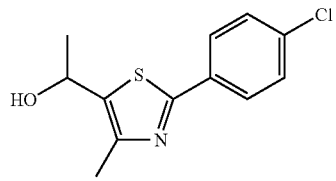

To a solution of methylketone intermediate 15 (2.5 g, 9.9 mmol) in EtOH (25 mL) was added at once NaBH$_4$ (750 mg, 20 mmol, 2 eq.) at 0° C. After stirring 3 hours at room temperature EtOH was removed under reduced pressure and 1N HCl was added. The resulting precipitate was filtered off, washed with water and dried under vacuum to afford the title compound (2.4 g, 9.4 mmol) in a 95% yield as a white solid.

$^1$H NMR (CDCl$_3$) δ: 1.56(d, 3H, J=6 Hz), 2.39 (s, 3H), 5.16(m, 1H), 7.37 (d, 2H, J=8.0 Hz), 7.79(d, 2H, J=8.0 Hz)

Intermediate 24:

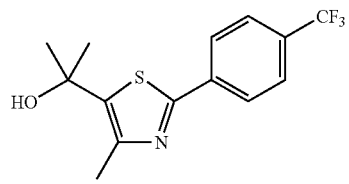

To a solution of ethyl-4-methyl-2-[4-(trifluoromethyl)-phenyl]-thiazole-5-carboxylate (2 g, 6.4 mmol) was added slowly at −10° C., a solution of 1.4M methylmagnesium bromide in toluene (10 mL, 14 mmol, 2 eq). The mixture was naturally warmed at room temperature and then stirred for 72 hours. The resulting mixture was quenched with saturated NH4Cl solution (100 mL) and extracted with EtOAc (2×250 mL). The organic phase was washed with brine and water, and then dried over Na$_2$SO$_4$ and evaporated off to give the title compound as a yellow solid (1 g, 3.3 mmol) in a 52% yield.

$^1$H NMR (CDCl$_3$) δ: 1.70 (s, 6H), 2.65 (s, 3H), 7.60 (d, 2H), 7.95 (d, 2H)

Intermediate 25:

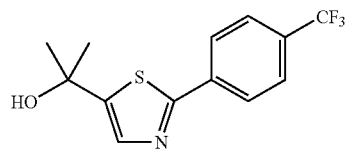

To a solution of intermediate 4 (750 mg, 2.5 mmol) was added slowly at −10° C., a solution of 1.4M methylmagnesium bromide in toluene (8.95 mL, 12.5 mmol, 5 eq). The mixture was naturally warmed at room temperature and then stirred for 24 hours. The resulting mixture was quenched with saturated NH4Cl solution (100 mL) and extracted with EtOAc (2×250 mL). The organic phase was washed with brine and water, and then dried over Na$_2$SO$_4$ and evaporated off to give the title compound (460 mg, 1.6 mmol) in a 64% yield after flash chromatography CH$_2$Cl$_2$/MeOH (99:1).

GC/MS: C$_{13}$H$_{12}$F$_3$NOS m/z: 287

Intermediate 26:

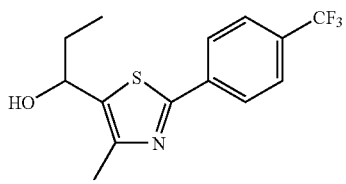

To a solution of intermediate 8 (4.05 g, 15 mmol) in 50 mL of THF was added slowly at −10° C., a solution of 3M ethylmagnesium bromide in Et$_2$O (5.5 mL, 16.5 mmol, 1.1 eq). The mixture was naturally warmed at room temperature and then stirred for 1.5 hour. The resulting mixture was quenched with saturated NH$_4$Cl solution (100 mL) and extracted with ethyl Acetate. The organic phase was washed with brine and water, and then dried over Na$_2$SO$_4$ and evaporated off. The residue was taken up with a mixture of isopropyl ether and petroleum ether. The white solid obtained was filtered to give the title compound (4.31 g, 14.3 mmol) in a 95% yield.

GC/MS: C$_{14}$H$_4$F$_3$NOS: m/z 301 mp: 104-106° C.

Intermediate 27:

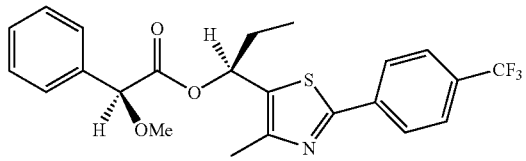

Intermediate 26 (8.23 g, 27.3 mmol) was added to a mixture of (R)-(−)-α-Methoxyphenylacetic acid (5 g, 30 mmol), DCC (6.18 g, 30 mmol) and DMAP (catalytic) in 250 ml THF. The mixture was stirred at room temperature 24 hours and passed through a plug of silica gel. The filtrate was concentrated to dryness and flash chromatographed using Petroleum ether/EtOAc (95:5). The less polar fraction was collected to afford 2.9 g of the title compound (2.9 g, 6 mmol).

$^1$H NMR(CDCl$_3$) δ: 0.73 (t, 3H), 1.83 (m, 2 H), 2.49 (s, 3H), 3.37 (s, 3H), 4.74 (s, 1H), 5.97 (t, 1H), 7.33 (m, 3H), 7.43 (m, 2H), 7.66 (d, 2H), 8.00 (d, 2H)

Intermediate 28:

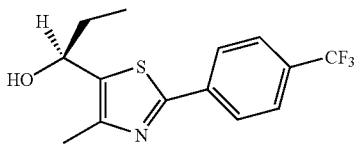

To a well-stirred solution of Intermediate 27 (2.75 g, 6 mmol) in THF/EtOH was added dropwise at 0° C. a solution of 18 mL of 1N NaOH in 15 mL of water. After 5 min the cleavage was completed and slowly at 0° C. was added 18 mL of 1 N HCl in 15 ml H$_2$O. The organic solvents were removed under reduced pressure and extraction with EtOAc (250 mL) washing with brine (25 mL) and drying over Na$_2$SO$_4$ gave a residue which was chromatograhed CH₂Cl₂/EtOAc (90:10) to afford in a 82% yield (1.49 g, 3.3 mmol) the title compound with an e.e.=98%.

GC/MS: C₁₄H₁₄F₃NOS m/z 301

$[α]^{25}_D$=−10 (c=0.279, CHCl₃) for e.e.=98%

HPLC Chiralpak AD-RH (4.6×150 mm, 65% CH₃CN/35% H₂O, 0.3 mL/min)

Rt: 21.2 min

Intermediate 29:

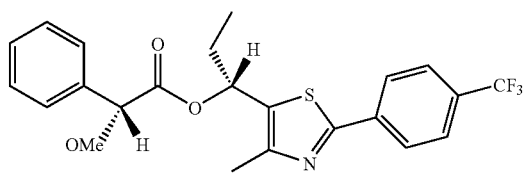

The same esterification protocol as described for intermediate 27 was applied with 10 g of racemic Intermediate 26 and 6 g of (S)-(+)-α-Methoxyphenylacetic acid to afford 2.85 g of the less polar diastereomer.

¹H NMR(CDCl₃) δ: 0.73 (t, 3H), 1.82 (m, 2H), 2.49 (s, 3H), 3.37 (s, 3H), 4.74 (s, 1H), 5.97 (t, 1H), 7.33 (m, 3H), 7.43 (m, 2H), 7.66 (d, 2H), 8.0(d, 2H)

Intermediate 30:

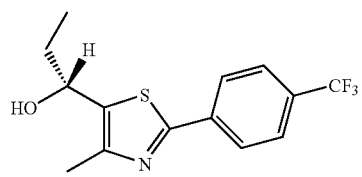

The same saponification protocol as used to obtain Intermediate 28 was applied to intermediate 29 (2.85 g, 6.35 mmol) to afford the title compound (1.58 g, 5.25 mmol) as a pale yellow oil in a 82.5% yield and with an e.e.=98%

¹H NMR(CDCl₃) δ: 0.98 (t, 3H), 1.96 (m, 2H), 2.45 (s, 3H), 4.92 (t, 1H), 7.66 (d, 2H), 8.0 (d, 2H)

$[α]^{25}_D$=+11 (c=0.29, CHCl₃) for e.e.=98%

HPLC Chiralpak AD-RH (4.6×150 mm, 65% CH₃CN/35% H₂O, 0.3 mL/min)

Rt: 25.04 min

Intermediate 31:

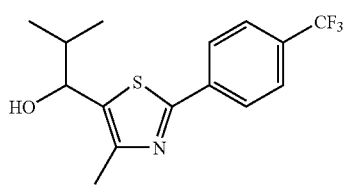

To a solution of intermediate 8 (2.71 g, 10 mmol) was added slowly at −12° C., a 2M solution of isopropylbromide magnesium in THF (5.5 ml, 11 mmol). The mixture was naturally warmed at room temperature and then stirred for 1.5 hour. The resulting mixture was quenched with saturated NH₄Cl solution (100 ml) and extracted with EtOAC (2×150 ml). The organic phase was washed with brine and water, and then dried over Na₂SO₄ and evaporated off to give the title compound (2 g, 6.34 mmol) in a 63.5% yield as a slightly yellow powder after crystallisation in hexane/Ethanol.

¹H NMR(CDCl₃, 300 MHz) δ: 0.8 (d, 3H), 1.05 (d, 3H), 1.9 (m, 1H), 2.35 (s, 3H), 4.55 (d, 1H), 7.6 (d, 2H), 7.95 (d, 2H)

Intermediate 32:

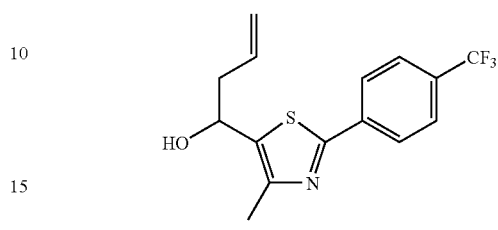

To a solution of intermediate 8 (5.42 g, 20 mmol) in 50 mL of THF was added slowly at −78° C., a 1M solution of allylmagnesium bromide in Et₂O (22 mL, 22 mmol, 1.1 eq). The mixture was stirred 30 minutes at −78° C. and was naturally warmed at RT and then stirred for 1 hour. The resulting mixture was quenched with saturated NH₄Cl solution (100 mL) and extracted with ethyl acetate. The organic phase was washed with brine and water, and then dried over Na₂SO₄ and evaporated off. The residue was taken up in heptane to yield the title compound after filtration as a white solid (5 g, 16 mmol) in a 80% yield.

LC/MS: C₁₅H₁₅F₃NOS: m/z 314.00 (M+1)

Intermediate 33:

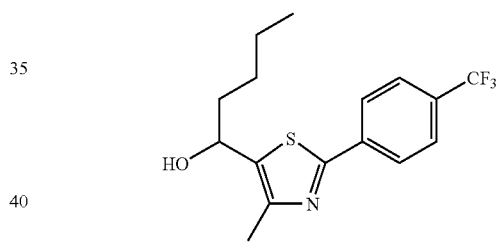

To a solution of intermediate 8 (813 mg, 3 mmol) was added slowly at −78° C., a 2M solution of butyl lithium in tetrahydrofuran (1.6 mL, 3 mmol). The mixture was naturally warmed at room temperature and then stirred for 1.5 hour. The resulting mixture was quenched with saturated NH₄Cl solution (100 mL) and extracted with EtOAc (2×100 mL). The organic phase was washed with brine and water, and then dried over Na₂SO₄ and evaporated off to give the title compound as a yellow solid (770 mg, 6.96 mmol) in a 99% crude yield.

¹H NMR(CDCl₃, 300 MHz) δ: 0.8 (t, 3H), 1.25 (m, 4H), 1.7 (m, 1H), 1.8 (m, 1H), 2.3 (s, 3H), 2.8 (brs, 1H), 4.9 (t, 1H), 7.55 (d, 2H), 7.9 (d, 2H)

mp 72-74° C.

Intermediate 34:

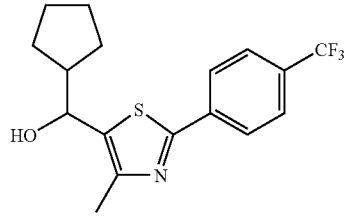

To a solution of intermediate 8 (5 g, 18.45 mmol) was added slowly at 0° C., a 2M solution of cyclopentylmagnesium bromide in Et₂O (11 mL, 22 mmol). The mixture was naturally warmed at room temperature and then stirred for 1.5 hour. The resulting mixture was quenched with saturated NH₄Cl solution (100 mL) and extracted with EtOAc (2×250 mL). The organic phase was washed with brine and water, and then dried over Na₂SO₄, evaporated off to give the title compound (2.2 g, 6.4 mmol) in a 35% yield after flash chromatography using C₆H₁₂/EtOAc (85:15)

LC/MS C₁₇H₁₉F₃NOS: m/z 342 (M+1)

Intermediate 35:

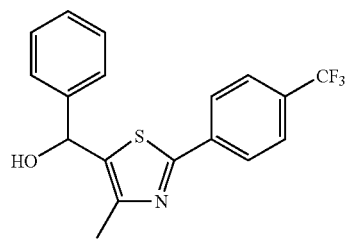

To a solution of intermediate 8 (1.4 g, 5.17 mmol) in 50 mL of THF was added slowly at −78° C., a 1M solution of phenylmagnesium bromide in THF (5.7 mL, 5.7 mmol, 1.1 eq). The mixture was stirred 30 min at −78° C. and was naturally warmed at room temperature and then stirred for 2 hours. The resulting mixture was quenched with saturated NH₄Cl solution and extracted with ethyl acetate. The organic phase was washed with water, dried over Na₂SO₄, evaporated off and the residue was crystallized in hexane. The white solid obtained was filtered and washed with hexane to give the title compound (1.7 g, 4.9 mmol) in a 86% yield.

GC/MS: C₁₈H₁₄F₃NOS m/z 349

Intermediate 36:

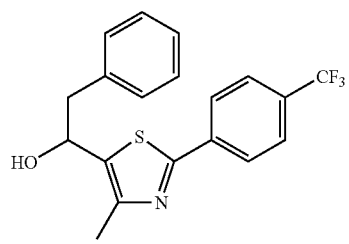

To a solution of intermediate 8 (4.48 g, 16.5 mmol) was added slowly at −10° C., a solution of 1.3M benzylmagnesium chloride in tetrahydrofuran (20 ml, 26.5 mmol, 1.6 eq). The mixture was naturally warmed at room temperature and then stirred for 1.5 hour. The resulting mixture was quenched with saturated NH₄Cl solution (100 mL) and extracted with Ethyl Acetate(2×250 mL). The organic phase was washed with brine and water, and then dried over Na₂SO₄ and evaporated off to give a pale yellow solid. After sonication in petroleum ether and filtration, the title compound (2.8 g, 7.7 mmol) was obtained in a 48% yield as a white powder.

LC/MS: C₁₉H₁₇F₃NOS m/z 364.13 (M+1)

mp: 126-129° C.

Intermediate 37:

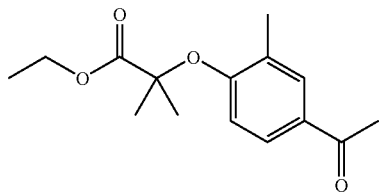

A suspension of 20 g (0.133 mole) of 4-acetyl-2-methylphenol and 30 g of potassium carbonate (0.2 mole) in 500 mL of acetone was heated at reflux for 24 hours. 30 mL of ethyl 2-bromo-2-methylpropionate in solution in 30 mL of acetone was added dropwise. The mixture was stirred at reflux during 20 hours and a tlc monitoring showed that the reaction was not complete. Then two supplementary equivalent portions of potassium carbonate and halide were added with a 7 hours interval. The mixture was stirred for 24 hours at reflux and stirred at room temperature for 2 days then filtered off and concentrated under vacuo. The residue was taken up with 300 mL of EtOAc and washed with 100 mL of 1N NaOH and 100 mL of brine. The organic layer was dried over Na₂SO₄, filtered and concentrated under vacuo to give 32.6 g of the title compound as a yellow oil in a 92% yield.

¹H NMR (CDCl₃): δ 1.19 (t, 3H), 1.63 (s, 6H), 2.24(s, 3H), 2.50 (s, 3H), 4.20 (q, 2H), 6.58 (d, 1H), 7.67 (d, 1H), 7.75 (s, 1H),

Intermediate 38:

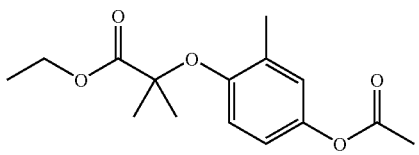

To a solution of 30 g (0.11 mole) of intermediate 37 in 300 mL of CH₂Cl₂ was added at once 2.2 g (0.011 mole) of p-toluenesulfonic acid and 35.9 g (0.125 mol) of m-chloroperbenzoic acid. The solution was heated at 50° C. for 21 hours then filtered and washed consecutively with a solution of 20 of KI in 200 mL of water, 20 g of Na₂SO₃ in 200 mL of water, 150 mL of 1N NaOH and 100 mL of brine. The organic layer was dried over Na₂SO₄, filtered and concentrated under vacuo to afford 28.54 g of the expected compound in a 89% yield.

GC/MS C₁₅H₂₀O₅: m/z 280

Intermediate 39:

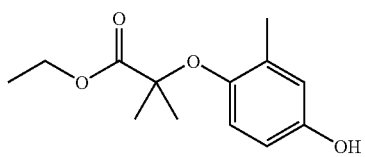

To a solution of 259 (0.089 mol) of intermediate 38 in 250 mL of anhydrous EtOH was added 9.1 g of NaOEt (0.134 mol). The solution was heated at 50° C. for 6 hours and concentrated under vacuo. The residue was taken up with 200 mL of water and acidified cautiously to pH=1 with 150 mL of 1N HCl. Extraction with 3×200 mL of EtOAc and drying of the gathered organic layers over MgSO$_4$ led after filtration and evaporation under vacuo to 21.62 g of the title compound.

GC/MS C$_{13}$H$_{18}$O$_4$: m/z 238

Intermediate 40:

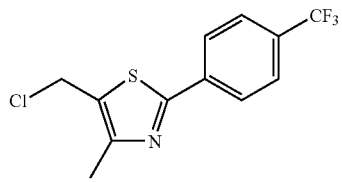

To a cold (0° C.) stirred solution of intermediate 1 (8.2 g, 30 mmol) and Et$_3$N (6.07 g, 8.36 mL, 60 mmol), in dry CH$_2$Cl$_2$ (120 mL) was slowly added MeSO$_2$Cl (5.49 g, 3.71 mL, 48 mmol). After 2 hours at 0° C. more Et$_3$N (6 mmol) and MeSO$_2$Cl (4.8 mmol) were added. After 2 more hours a tic (hexane: EtOAc, 1:1) showed complete reaction. The reaction mixture was diluted with CH$_2$Cl$_2$ (120 mL) and washed with NaHCO$_3$ (sat.) (2×240 mL) and water (2×240 mL), dried, filtered and evaporated to afford the title compound (8.0 g, 27 mmol, 90%) as a yellow solid.

Intermediate 41:

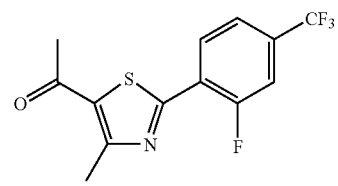

A solution of 2-fluoro-4-trifluoromethyl-thiobenzamide (1.02 g, 4.57 mmol) and 3-chloro-pentane-2,4-dione (654 µL, 5.5 mmol) in 30 mL of EtOH was heated to reflux during 18 hours. A supplementary 1.2 equivalent of 3-chloro-pentane-2,4-dione (654 µL, 5.5 mmol) was added, the reaction heated to reflux for an additional 18 hours and evaporated to dryness. The residue was diluted with 250 mL of CH$_2$Cl$_2$ and washed with 50 mL of saturated solution of NaHCO$_3$. The organic phase was separated, dried over Na$_2$SO$_4$, filtered and concentrated under vacuo to give the title compound (850 mg, 12 mmol) in a 61% yield as a yellow solid after flash chromatography CH$_2$Cl$_2$.

GC/MS C$_{13}$H$_9$F$_4$NOS m/z 303

Intermediate 42:

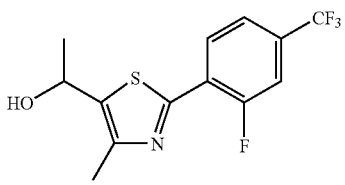

To a solution of methylketone intermediate 41 (850 mg, 2.8 mmol) in EtOH (50 mL) was added at once NaBH$_4$ (117 mg, 3 mmol, 1.1 eq.) at 0° C. After stirring 30 minutes at room temperature MeOH was removed under reduced pressure, 1N HCl was added and extraction with Et$_2$O (2×100 mL) followed by drying over Na$_2$SO$_4$ and filtration afforded the title compound (770 mg, 2.53 mmol) in a 90% yield as a pale yellow solid.

GC/MS C$_{13}$H$_{11}$F$_4$NOS m/z 305

Intermediate 43:

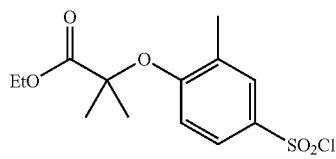

To a solution of chlorosulfonic acid (90 mL, 4.4 eq.) was added dropwise at 0° C. in 1 hour 2-Methyl-2-o-tolyloxy-propionic acid ethyl ester (68 g, 0.306 mol). After stirring for 1 hour at 0° C. and an additional 30 min at 15° C. the mixture was poured into crushed ice and the precipitate thus obtained was filtered and washed with cold water. The title compound was obtained as an off white powder (62.2 g, 0.194 mol) in a 63% yield.

GC/MS: C$_{13}$H$_{17}$ClO$_5$S m/z: 320.5

Intermediate 44:

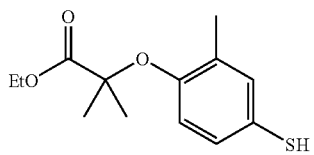

In a three neck round bottom flask under a nitrogen atmosphere containing Zn (13.1 g, 0.2 mol, 3.5 eq) in dry EtOAc (150 mL) was added intermediate 43 (18.32 g, 0.057 mol). After stirring for 30 min, dichloromethylsilane (24.4 mL, 0.2 mol, 3.5 eq) was added slowly in 90 min at 70° C. After stirring for 5 hours at 70° C. a supplementary portion of Zn (3 g, 45 mmol) was added to complete the reaction. Then the resulting mixture was stirred overnight filtered and the zinc precipitate washed with EtOAc. A back extraction was carried out on the filtrate with 1N NaOH (3×300 mL) and the gathered basic phases were washed with EtOAc (400 mL). Acidification of basic aqueous phases to pH=3-4 with concentrated HCl, extraction with EtOAc (3×300 mL), drying of the organic phase over MgSO$_4$, filtration and concentration to dryness gave a colorless oil. The title compound (10.01 g, 39.4 mmol) was obtained after flash chromatography C$_6$H$_{12}$/EtOAc (90:10) as a colorless oil in a 69% yield.

GC/MS: C$_{13}$H$_{18}$O$_3$S m/z: 254

EXAMPLE 1

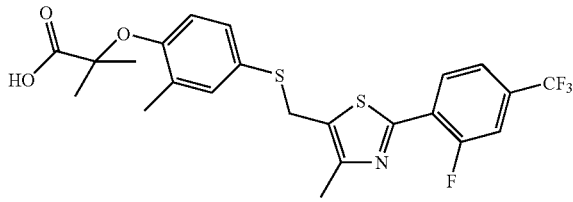

2-{4-[({2-[2-fluoro-4-(trifluoromethyl)phenyl]-4-methyl-1,3-thiazol-5-yl}methyl)sulfanyl]-2-methylphenoxy}-2-methylpropanoic acid To a 25 ml round-bottom flask equipped with a magnetic stir-bar and $N_2$ inlet was added intermediate 7 (240 mg, 0.58 mmol, 1 eq) in acetone (4 ml) followed by the addition of 2-trichloromethyl-2-propanol (210 mg, 1.18 mmol, 2 eq). The reaction was cooled to 0° C. and then NaOH (pellets, 190 mg, 4.8 mmol, 8 eq) were added. The reaction mixture warmed to room temperature and stirred at room temperature overnight after which the acetone was removed in vacuo and the resulting residue was partitioned between EtOAc and water acidified to pH2 with conc. HCl. The phases were then separated and the organic fraction was washed with brine, dried over $MgSO_4$ and concentrated in vacuo to yield after chromatography (0.05 g, 17%) of the title compound as a cream colored solid.

$^1$H NMR (CD$_3$OD): δ 1.59 (s, 6H), 2.17 (s, 3H), 2.20 (s, 3H), 4.24 (s, 2H), ), 6.72 (d, 1H), 7.12 (d, 1H), 7.20 (s, 1H), 7.65 (m, 2H), 8.38 (t, 1H)

MS $C_{23}H_{22}F_4NO_3S_2$ m/z 500 (M+1).

EXAMPLE 2

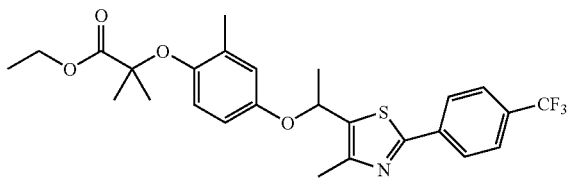

2-methyl-2-(2-methyl-4-{1-[4-methyl-2-(4-trifluoromethylphenyl)-thiazol-5-yl]ethoxy}phenoxy)propionic acid ethyl ester To a solution of intermediate 39 (238 mg, 1 mmol) and intermediate 16 (287 mg, 1 mmol, 1 eq) in dry THF was added PBu$_3$ (0.37 mL, 1.5 mmol, 1.5 eq). The resulting mixture was stirred at 0° C., and then TMAD (258 mg, 1.5 mmol, 1.5 eq) was added all at once. The mixture was stirred at 0° C. for 10 minutes, and at room temperature for 24 hours. The resulting mixture was filtered off and concentrated in vacuo, and the title compound was obtained as a yellow oil (270 mg, 0.532 mmol) in a 53% yield after flash chromatography using cyclohexane/ethyl acetate (95:5) as eluent.

MS: $C_{26}H_{29}F_3NO_4S$ m/z 507.96 (M+1)

EXAMPLE 3

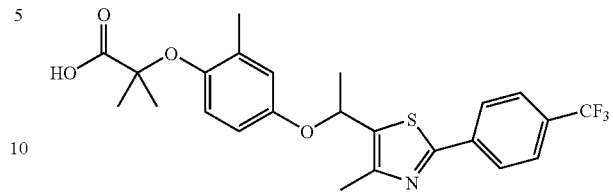

2-methyl-2-(2-methyl-4-{1-[4-methyl-2-(4-trifluoromethylphenyl)-thiazol-5-yl]ethoxy}phenoxy)propionic acid To a solution of Example 2 (200 mg, 0.394 mmol) in ethanol was added 1N NaOH (5 mmol, 12.7 eq). The resulting mixture was stirred at 80° C. for 1.5 hour, and after cooling at room temperature 1N HCl (5 mmol, 12.7 eq) was added. The resulting mixture was concentrated in vacuo and the residue was purified by flash chromatography using $CH_2Cl_2$/MeOH (95:5) as eluent to give an oil. The product was crystallized with a mixture of water/EtOH/MeOH, filtered off and washed with water to give the title compound (50 mg, 0.104 mmol) in a 26% yield.

LC/MS: $C_{24}H_{25}F_3NO_4S$ m/z 480.25 (M+1)/ $C_{24}H_{23}F_3NO_4S$: m/z 478.31 (M−1)

EXAMPLE 4

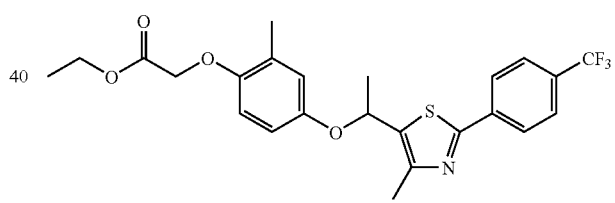

(2-methyl-4-{1-[4-methyl-2-(4-trifluoromethylphenyl)-thiazol-5-yl]ethoxy}-phenoxy)-acetic acid ethyl ester A solution of ethyl (4-hydroxy-2-methylphenoxy)acetate (0.073 g) and intermediate 16 (100 mg) in dry tetrahydrofuran (20 mL) was cooled to 0° C. and tributylphosphine (0.092 mg) added followed by azodicarbonyldimorpholide (0.115 g) and the mixture stirred overnight. The reaction mixture was then concentrated and the residue partitioned between EtOAc (40 mL) and water (40 mL). The organic phase was collected, dried over magnesium sulphate and concentrated. The residue was purified by chromatography eluting with cyclohexane/ethyl acetate (10:1) to give the title compound as a colourless oil $^1$H NMR(CDCl$_3$, 300 MHz) δ: 1.27 (t, 3H), 1.70 (d, 3H),), 2.24 (s, 3H),), 2.45 (s, 3H), 4.24 (q, 2H), 4.54 (s, 2H), 5.47 (q, 1H), 6.60 (m, 2H), 6.75 (d, 1H), 7.65 (d, 2H), 7.98 (d, 2H)

EXAMPLE 5

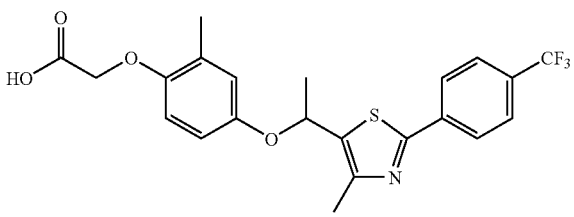

(2-methyl-4-{1-[4-methyl-2-(4-trifluoromethylphenyl)-thiazol-5-yl]ethoxy}-phenoxy)-acetic acid A solution of example 4 (0.105 g) in methanol (15 mL) was treated with 2N NaOH (0.5 mL) and the mixture heated to reflux for 20 minutes. The cooled reaction was concentrated and the residue diluted with water (20 mL) 2N hydrochloric acid was added and the resulting suspension extracted with dichloromethane (20 mL). The organic extract was dried over $MgSO_4$ and concentrated to give the title compound as a yellow solid.

$^1$H NMR(CDCl$_3$, 300 Mhz) δ: 170 (d, 3H), 2.22 (s, 3H), 2.44 (s, 3H), 4.58 (s, 2H), 5.47 (q, 1H), 6.60 (m, 2H), 6.75 (s, 1H), 7.65 (d, 2H), 7.95 (d, 2H)

LC/MS $C_{22}H_{21}F_3NO_4S$ m/z 452 (M+1)

EXAMPLE 6

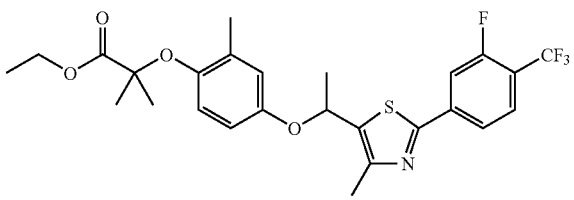

2-methyl-2-(2-methyl-4-{1-[4-methyl-2-(3-fluoro-4-trifluoromethylphenyl)-thiazol-5-yl]ethoxy}-phenoxy)-propionic acid ethyl ester To a solution of PBu$_3$ (460 µL, 1.5 eq) and TMAD (321 mg, 1.5 eq) in dry THF (50 mL) were added intermediate 39 (356 mg, 1.4 mmol) and intermediate 20 (380 mg, 1.24 mmol, 1.1 eq). The resulting mixture was stirred to room temperature for 18 hrs and was concentrated to dryness to afford the title compound (270 mg, 0.51 mmol) as a colorless oil after flash chromatography $CH_2Cl_2/C_6H_{12}$ (80:20).

$^1$H NMR(CDCl$_3$) δ: 1.15 (t, 3H), 1.35 (s, 6H), 1.62 (d, 3H), 2.08 (s, 3H), 2.34 (s, 3H), 4.12 (q, 2H), 5.38 (q, 1H), 6.45 (dd, 1H), 6.51 (d, 1H), 6.6 (d, 1H), 7.52 (d, 2H), 7.63 (d, 2H),

EXAMPLE 7

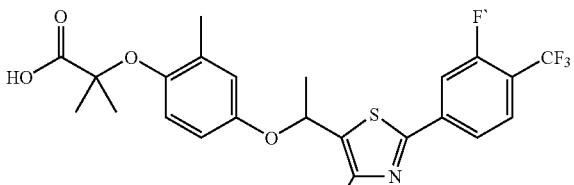

2-methyl-2-(2-methyl-4-{1-[4-methyl-2-(3-fluoro-4-trifluoromethylphenyl)-thiazol-5-yl]ethoxy}-phenoxy)-propionic acid A solution of example 6 (270 mg) in EtOH (15 mL) was treated with 1N sodium hydroxide (1.54 mL, 3 eq.) and the mixture heated to reflux for 3 hours. The cooled reaction was concentrated and the residue diluted with water (20 mL); 1N hydrochloric acid (2 mL) was added and the resulting suspension extracted with dichloromethane (20 mL). The organic extract was dried over magnesium sulphate and concentrated to give the title compound in 74% yield as a yellow solid (190 mg).

$^1$H NMR(CDCl$_3$) δ: 1.80 (s, 6H), 1.95 (d, 3H), 2.43 (s, 3H), 2.70 (s, 3H), 5.82 (q, 1H), 6.82 (dd, 1H), 6.97 (m, 2H), 7.85 (m, 1H), 7.95 (m, 2H),

LC/MS: $C_{24}H_{22}F_4NO_4S$ m/z 495.7 (M−1)

EXAMPLE 8

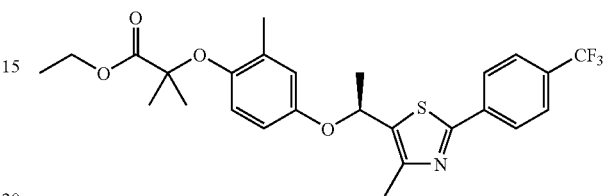

(S)-2-methyl-2-(2-methyl-4-{1-[4-methyl-2-(4-trifluoromethylphenyl)-thiazol-5-yl]ethoxy}-phenoxy)-propionic acid ethyl ester The same Mitsunobu protocol as described for example 2 was applied with intermediate 18 (1.722 g, 6 mmol; e.e.=95.5%) and intermediate 39 (1.43 g, 6 mmol, 1 eq.). The title compound was obtained as a pale yellow oil (1.6 g, 3.15 mmol) in a 52.5% yield.

$^1$H NMR (CDCl$_3$, 300 MHz) δ: 1.15 (t, 3H), 1.44 (s, 6H), 1.61 (d, 3H), 2.09 (s, 3H), 2.36 (s, 3H), 4.13 (q, 2H), 5.39 (q, 1H), 6.47 (dd, 1H), 6.53 (d, 1H), 6.63 (d, 1H), 7.57 (d, 2H), 7.90 (d, 2H)

EXAMPLE 9

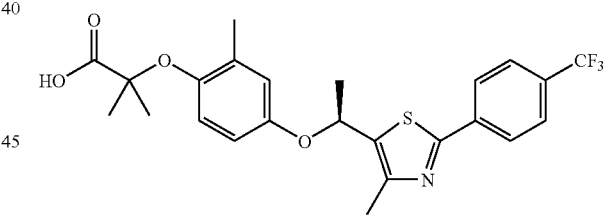

(S)-2-methyl-2-(2-methyl-4-{1-[4-methyl-2-(4-trifluoromethylphenyl)-thiazol-5-yl]ethoxy}-phenoxy)-propionic acid The same saponification protocol as for example 3 was applied using 1.6 g of Example 8 (1.6 g, 3.15 mmol). The white powder obtained after work up was recrystallized in Hexane/EtOH to give the title compound as a white powder (780 mg, 1.628 mmol) in a 52.5% yield with an e.e.=99.9% mp 134-135° C.

$^1$H NMR (CDCl$_3$) δ: 1.41 (s, 6H), 1.58 (d, 3H), 2.06 (s, 3H), 2.33 (s, 3H), 5.36 (q, 1H), 6.46 (dd, 1H), 6.61 (m, 2H), 7.50 (d, 2H), 7.82 (d, 2H)

$[\alpha]^{25}_D$=−169.9 (c=0.275, CHCl$_3$) for e.e.=99.9%

HPLC Chiralpak AD (4.6×250 mm, 95% Hexane/5% EtOH) Rt: 8.79 min

EXAMPLE 10

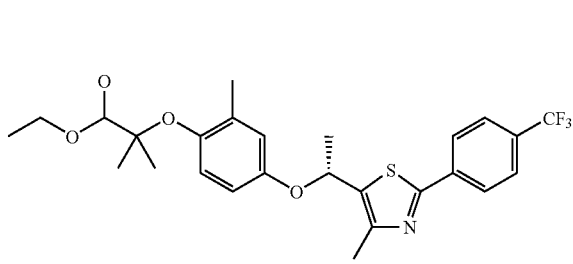

(R)-2-methyl-2-(2-methyl-4-{1-[4-methyl-2-(4-trifluoromethylphenyl)-thiazol-5-yl]ethoxy}-phenoxy)-propionic acid ethyl ester The same Mitsunobu protocol as described for example 2 was applied with Intermediate 19 (1.4 g, 4.9 mmol e.e.=98%) and intermediate 39 (1.17 g, 4.9 mmol). The title compound was obtained as a pale yellow oil (1.4 g, 2.9 mmol ) in a 60% yield.

$^1$H NMR (CDCl$_3$) δ: 1.04 (t, 3H), 1.33 (s, 6H), 1.50 (d, 3H), 1.98 (s, 3H), 2.25 (s, 3H), 4.02 (q, 2H), 5.27 (q, 1H), 6.35 (dd, 1H), 6.42 (d, 1H), 6.52 (d, 1H), 7.46 (d, 2H), 7.80 (d, 2H)

EXAMPLE 11

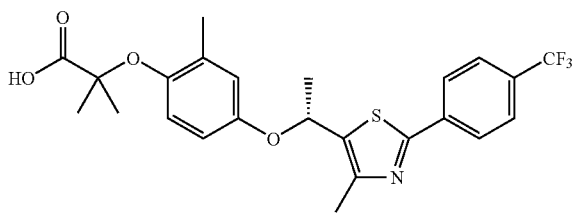

(R)-2-methyl-2-(2-methyl-4-{1-[4-methyl-2-(4-trifluoromethylphenyl)-thiazol-5-yl]ethoxy}-phenoxy)-propionic acid The same saponification protocol as described for example 3 was applied using Example 10 (400 mg, 0.79 mmol). The residue was purified by flash chromatography CH$_2$Cl$_2$/MeOH (99:1) to give the title compound (220 mg, 0.458 mmol) as a pale yellow oil in a 58% yield with an e.e.=87%

$^1$H NMR (CDCl$_3$, 300 MHz) δ: 1.47 (s, 6H), 1.63 (d, 3H), 2.12 (s, 3H), 2.38 (s, 3H), 5.42 (q, 1H), 6.52 (dd, 1H), 6.67 (m, 2H), 7.56 (d, 2H), 7.90 (d, 2H)

$[α]^{25}_D$=+142 (c=0.37, CHCl$_3$ ) for ee=87%

HPLC: Chiralpak-AD (4.6×250 mm, 95% Hexane/5% EtOH ) Rt: 15 min

LC/MS: C$_{24}$H$_{25}$F$_3$NO$_4$S m/z 480.0 (M+1)

EXAMPLE 12

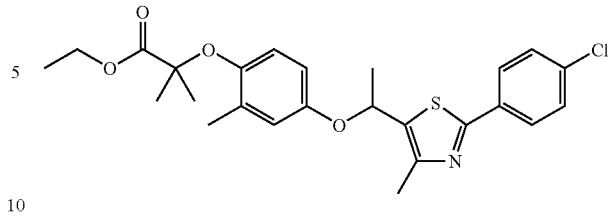

2-(4-{1-[2-(4-chloro-phenyl)-4-methyl-thiazol-5-yl]-ethoxy}-2-methyl-phenoxy)-2-methyl-propionic acid ethyl ester The same Mitsunobu conditions as described for racemic example 2 were applied to Intermediate 23 (520 mg, 2 mmol) and Phenol Intermediate 39 (530 mg, 2.2 mmol) and afforded in a 33% yield the title compound (320 mg, 0.67 mmol) as a colorless oil.

$^1$H NMR (CDCl$_3$) δ: 1.15 (t, 3H), 1.44 (s, 6H), 1.60 (d, 3H), 2.09 (s, 3H), 2.33 (s, 3H), 4.13 (q, 2H), 5.36 (q, 1H), 6.46 (dd, 1H), 6.52 (d, 1H), 6.62 (d, 1H), 7.27 (d, 2H), 7.72 (d, 2H)

EXAMPLE 13

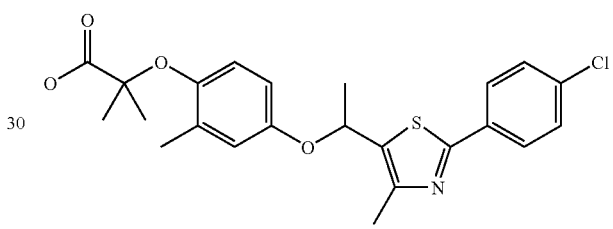

2-(4-{1-[2-(4-chloro-phenyl)-4-methyl-thiazol-5-yl]-ethoxy}-2-methyl-phenoxy)-2-methyl-propionic acid The same saponification conditions as described for racemic example 3 were applied to example 12 (320 mg, 0.67 mmol) and gave in a 70% yield the title compound (210 mg, 0.47 mmol).

LC/MS: C$_{23}$H$_{23}$ClNO$_4$S m/z 444.1 (M−1)
LC/MS: C$_{23}$H$_{25}$ClNO$_4$S m/z 446 (M+1)

EXAMPLE 14

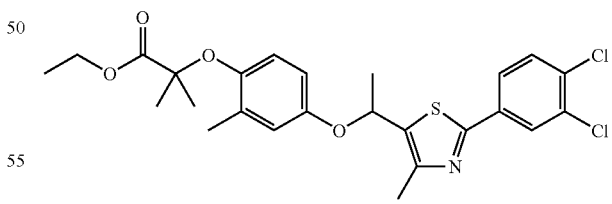

2-(4-{1-[2-(3,4-dichloro-phenyl)-4-methyl-thiazol-5-yl]-ethoxy}-2-methyl-phenoxy)-2-methyl-propionic acid ethyl ester The same Mitsunobu conditions as described for racemic example 2 were applied to Intermediate 22 (580 mg, 2 mmol) and Phenol Intermediate 39 (530 mg, 2.2 mmol) and afforded in a 42% yield the title compound (430 mg, 0.84 mmol) as a colorless oil.

¹H NMR (CDCl₃) δ: 1.15 (t, 3H), 1.43 (s, 6H), 1.59 (d, 3H), 2.09 (s, 3H), 2.33 (s, 3H), 4.13 (q, 2H), 5.37 (q, 1H), 6.46 (dd, 1H), 6.52 (d, 1H), 6.63 (d, 1H), 7.36 (d, 1H), 7.59 (dd, 1H), 7.91 (d, 1H)

EXAMPLE 15

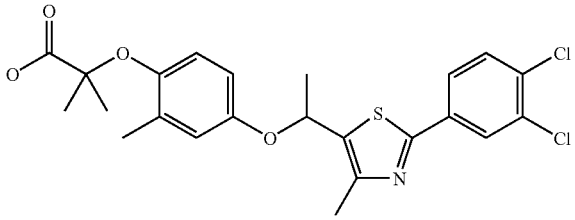

2-(4-{1-[2-(3,4-dichloro-phenyl)-4-methyl-thiazol-5-yl]-ethoxy}-2-methyl-phenoxy)-2-methyl-propionic acid The same saponification conditions as described for racemic example 3 were applied to example 14 (480 mg, 0.94 mmol) and gave in a 67% yield the title compound (300 mg, 0.63 mmol).

LC/MS: $C_{23}H_{22}Cl_2NO_4S$ m/z 478 and 480 (M−1)

EXAMPLE 16

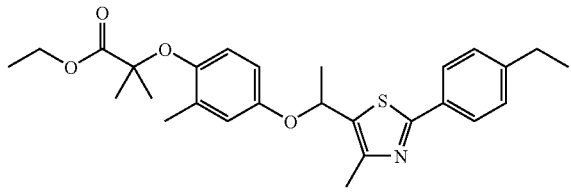

2-(4-{1-[2-(4-ethyl-phenyl)-4-methyl-thiazol-5-yl]-ethoxyl}-2-methyl-phenoxy)-2-methyl-propionic acid ethyl ester The same Mitsunobu conditions as described for racemic example 2 were applied to Intermediate 21 (500 mg, 2 mmol) and Phenol Intermediate 39 (530 mg, 2.2 mmol) and afforded in a 30% yield the title compound (280 mg, 0.6 mmol) as a colorless oil.

¹H NMR (CDCl₃) δ: 1.25 (m, 6H), 1.53 (s, 6H), 1.70 (d, 3H), 2.19 (s, 3H), 2.42 (s, 3H), 4.23 (q, 2H), 5.46 (q, 1H), 6.57 (dd, 1H), 6.62 (d, 1H), 6.73 (d, 1H), 7.23 (d, 2H), 7.81 (d, 2H)

EXAMPLE 17

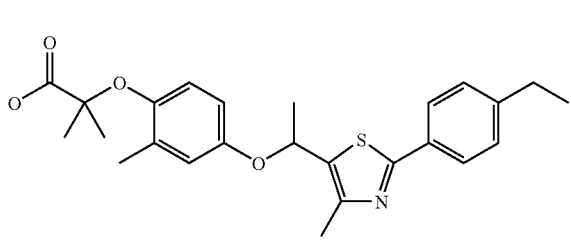

2-(4-{1-[2-(4-ethyl-phenyl)-4-methyl-thiazol-5-yl]-ethoxy}-2-methyl-phenoxy)-2-methyl-propionic acid The same saponification conditions as described for racemic example 3 were applied to example 16 (280 mg, 0.6 mmol) and gave in a 76% yield the title compound (200 mg, 0.45 mmol).

LC/MS: $C_{25}H_{30}NO_4S$ m/z 440.0 (M+1)

EXAMPLE 18

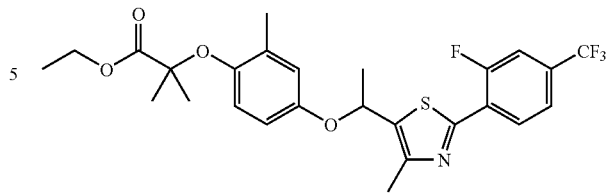

2-(4-{1-[2-(2-fluoro-4-trifluoromethyl-phenyl)-4-methyl-thiazol-5-yl]-ethoxy}-2-methyl-phenoxy)-2-methyl-propionic acid ethyl ester The same Mitsunobu conditions as described for racemic example 2 were applied to Intermediate 42 (400 mg, 1.31 mmol) and Phenol Intermediate 39 (312 mg, 1.31 mmol) and afforded in a 35% yield the title compound (240 mg, 0.456 mmol) as a colorless oil.

¹H NMR (CDCl₃) δ: 1.16 (t, 3H), 1.44 (s, 6H), 1.63 (d, 3H), 2.1 (s, 3H), 2.38 (s, 3H), 4.14 (q, 2H), 5.42 (q, 1H), 6.47 (dd, 1H), 6.52 (d, 1H), 6.65 (d, 1H), 7.38 (d, 2H), 8.3 (m, 1H)

EXAMPLE 19

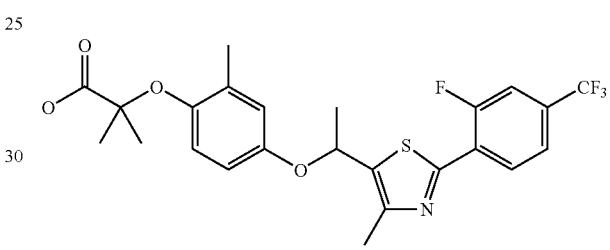

2-(4-{1-[2-(2-fluoro-4-trifluoromethyl-phenyl)-4-methyl-thiazol-5-yl]-ethoxy}-2-methyl-phenoxy)-2-methyl-propionic acid The same saponification conditions as described for racemic example 3 were applied to example 18 (240 mg, 0.46 mmol) and gave in a 97% yield the title compound as a white powder (220 mg, 0.442 mmol).

mp 133° C.

LC/MS: $C_{24}H_{22}F_4NO_4S$ m/z 495.9 (M−1)

EXAMPLE 20

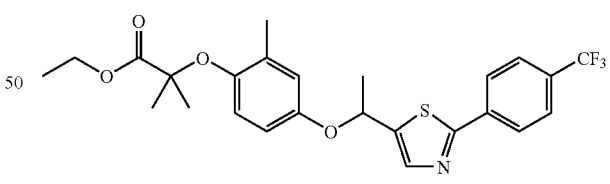

2-methyl-2-(2-methyl-4-{1-[2-(4-trifluoromethyl-phenyl)-thiazol-5-yl]-ethoxy}-phenoxy)-propionic acid ethyl ester The same Mitsunobu conditions as described for racemic example 2 were applied to Intermediate 17 (400 mg, 1.46 mmol) and phenol Intermediate 39 (349 mg, 1.46 mmol) and afforded in a 21% yield the title compound (150 mg, 0.303 mmol) as a colorless oil.

¹H NMR (CDCl₃) δ: 1.17 (t, 3H), 1.45 (s, 6H), 1.67 (d, 3H), 2.11 (s, 3H), 4.14 (q, 2H), 5.46 (q, 1H), 6.55 (s, 2H), 6.69 (br s, 1H), 7.60 (d, 2H), 7.66 (s, 1H), 7.95 (d, 2H)

EXAMPLE 21

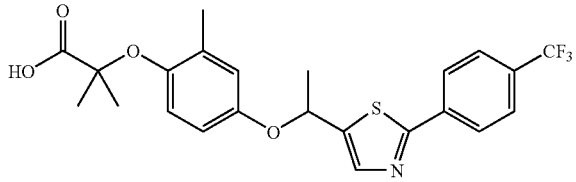

2-methyl-2-(2-methyl-4-{1-[2-(4-trifluoromethyl-phenyl)-thiazol-5-yl]-ethoxy}-phenoxy)-propionic acid The same saponification conditions as described for racemic example 3 were applied to example 20 (150 mg, 0.3 mmol) and gave in a 64% yield the title compound as a yellow powder (90 mg, 0.193 mmol).
LC/MS: $C_{23}H_{23}F_3NO_4S$ m/z 465.99 (M+1)

EXAMPLE 22

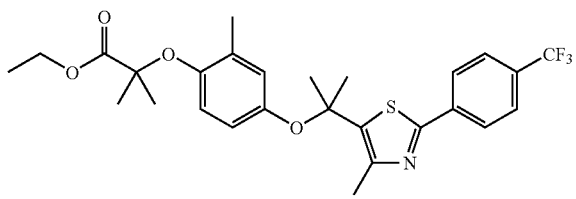

2-methyl-2-(2-methyl-4-{1-methyl-1-[4-methyl-2-(4-trifluoromethyl-phenyl)-thiazol-5-yl]-ethoxy}-phenoxy)-propionic acid ethyl ester The same Mitsunobu conditions as described for racemic example 2 were applied to Intermediate 24 (500 mg, 1.66 mmol) and phenol Intermediate 39 (440 mg, 1.85 mmol) and afforded in a 70% yield the title compound (610 mg, 1.17 mmol) as an oil after purification by flash chromatography $CH_2Cl_2$.
$^1$H NMR (CDCl$_3$) δ: 1.20 (t, 3H), 1.50 (s, 6H), 1.72 (s, 6H), 2.11 (s, 3H), 2.56 (s, 3H), 4.18 (q, 2H), 6.45 (dd, 1H), 6.49 (d, 1H), 6.64 (d, 1H), 7 64 (d, 2H), 7.96 (d, 2H),

EXAMPLE 23

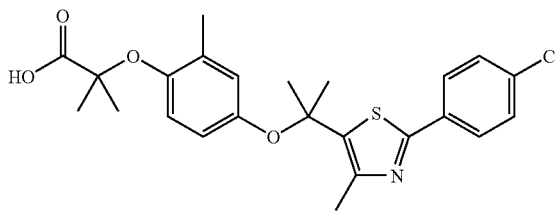

2-methyl-2-(2-methyl-4-{1-methyl-1-[4-methyl-2-(4-trifluoromethyl-phenyl)-thiazol-5-yl]-ethoxy}-phenoxy)-propionic acid The same saponification conditions as described for racemic example 3 were applied to example 22 (300 mg, 0.58 mmol) and gave in a 20% yield the title compound as a yellow powder (60 mg, 0.12 mmol).

LC/MS: $C_{25}H_{27}F_3NO_4S$ m/z 494.0 (M+1)

EXAMPLE 24

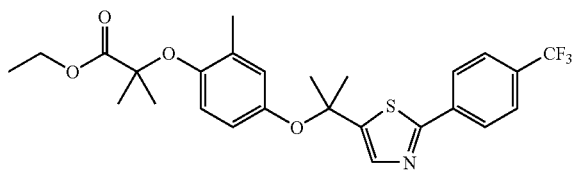

2-methyl-2-(2-methyl-4-{1-methyl-1-[2-(4-trifluoromethyl-phenyl)-thiazol-5-yl]-ethoxy}-phenoxy)-propionic acid ethyl ester The same Mitsunobu conditions as described for racemic example 2 were applied to Intermediate 25 (460 mg, 1.6 mmol) and phenol Intermediate 39 (381 mg, 1.85 mmol) and afforded in a 13.5% yield the title compound (110 mg, 1.17 mmol) as an oil after purification by flash chromatography $C_6H_{12}$/EtOAc (80:20)

$^1$H NMR (CDCl$_3$) δ: 1.15 (t, 3H), 1.46 (s, 6H), 1.50 (s, 3H), 1.68 (s, 6H), 2.06 (s, 3H), 4.13 (q, 2H), 5.46 (q, 1H), 6.55 (s, 2H), 6.69 (br s, 1H), 7.60 (d, 2H), 7.66 (s, 1H), 7.95 (d, 2H)

EXAMPLE 25

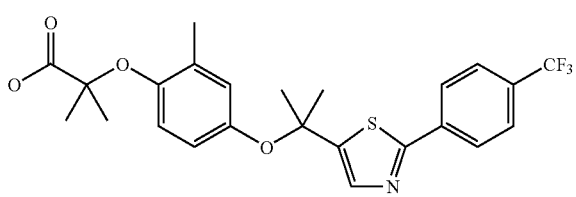

2-methyl-2-(2-methyl-4-{1-methyl-1-[2-(4-trifluoromethyl-phenyl)-thiazol-5-yl]-ethoxy}-phenoxy)-propionic acid The same saponification conditions as described for racemic example 3 were applied to example 24 (110 mg, 0.217 mmol) and gave in a 58% yield the title compound as a brown oil (60 mg, 0.125 mmol).

LC/MS: $C_{24}H_{23}F_3NO_4S$ m/z 478.1 (M−1)

EXAMPLE 26

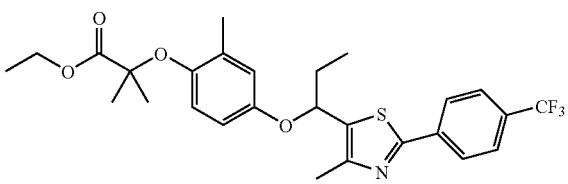

2-methyl-2-(2-methyl-4-{1-[4-methyl-2-(4-trifluoromethylphenyl)-thiazol-5-yl]propoxy}phenoxy) propionic acid ethyl ester To a solution of intermediate 39 (1.03 g, 4.3 mmol) and intermediate 26 (1.24 g, 4.3 mmol, 1 eq) in dry toluene was added PBu$_3$ (1.6 mL, 6.45 mmol, 1.5 eq). The resulting mixture was allowed to stir at 0° C., and then TMAD (1.11 g, 6.45 mmol, 1.5 eq) was added. The mixture was stirred at 0° C. for 1 hour, and at room temperature for 24 hours. The resulting mixture was filtered off, concentrated in vacuo, to afford after flash chromatography (cyclohexane/EtOAc: 95/5) the title compound as a yellow oil (1.3 g, 2.49 mmol) in a 58% yield.
LC/MS: $C_{27}H_{31}F_3NO_4S$ m/z 522.19 (M+1)

EXAMPLE 27

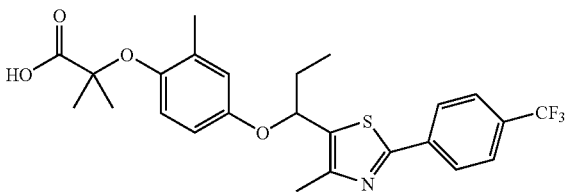

2-methyl-2-(2-methyl-4-{1-[4-methyl-2-(4-trifluoromethylphenyl)-thiazol-5-yl]propoxy}phenoxy) propionic acid To a solution of example 26 (1.1 g, 2.17 mmol) in THF/ethanol (1/1) was added 1N NaOH (10 mmol, 4.6 eq). The resulting mixture was stirred at 80° C. for 1.5 hour, and after cooling at room temperature 1N HCl (10 mmol, 4.6 eq) was added. The resulting mixture was concentrated in vacuo, and the residue was sonicated in water/EtOH. The resulting solid was filtered off and washed with water, diluted HCl, and water to give the title compound (680 mg, 1.38 mmol) in a 64% yield as a white powder.
LC/MS: $C_{15}H_{27}F_3NO_4S$: m/z 493.79 (M+1)

EXAMPLE 28

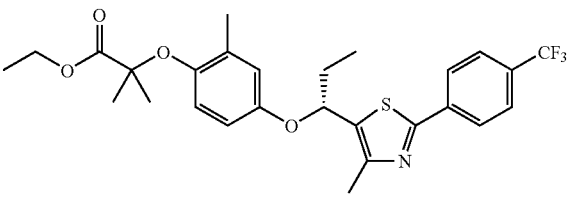

(R)-2-methyl-2-(2-methyl-4-{1-[4-methyl-2-(4-trifluoromethyl-phenyl)-thiazol-5-yl]propoxy}-phenoxy)-propionic acid ethyl ester The same Mitsunobu conditions as described for racemic example 2 were applied to intermediate 28 (1.4 g, 4.65 mmol; e.e.=98%) and phenol intermediate 39 (1.11 g, 4.65 mmol) and gave in a 54% yield the title compound (1.3 g, 2.5 mmol) with an e.e.=89%.
MS: $C_{27}H_{31}F_3NO_4S$ m/z: 522.1 (M+1)
$[\alpha]^{25}_D$=+147.5 (c=0.268, CHCl$_3$) for ee=89%
HPLC: Chiralpak-AD (4.6×250 mm, 95% Hexane/5% EtOH) Rt: 8.98 min

EXAMPLE 29

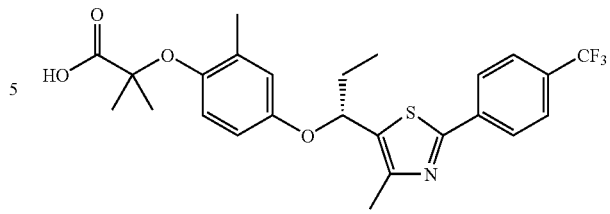

(R)-2-methyl-2-(2-methyl-4-{1-[4-methyl-2-(4-trifluoromethyl-phenyl)-thiazol-5-yl]propoxy}-phenoxy)-propionic acid The same saponification conditions as described for racemic example 3 were applied to example 28 (1.245 g, 2.4 mmol, e.e.=89%) and gave in a 68% yield the title compound as a white powder (800 mg, 1.6 mmol) with an e.e.=89%.
MS: $C_{25}H_{27}F_3NO_4S$: m/z 494.1 (M+1)
$[\alpha]^{25}_D$=+145.2 (c=0.259, CHCl$_3$) for e.e.=89%
HPLC: Chiralpak-AD (4.6×250 mm, 95% Hexane/5% EtOH ) Rt: 15.88 min

EXAMPLE 30

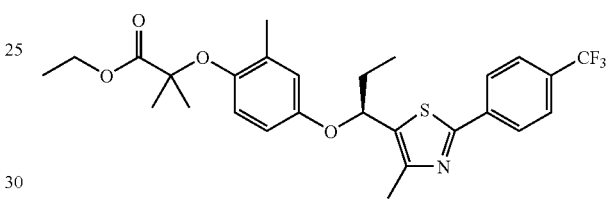

(S)-2-methyl-2-(2-methyl-4-{1-[4-methyl-2-(4-trifluoromethyl-phenyl)-thiazol-5-yl]propoxy}-phenoxy)-propionic acid ethyl ester The same Mitsunobu conditions as described for racemic example 2 were applied to (R)-alcohol intermediate 30 (1.58 g, 5.2 mmol, e.e.=98%) and phenol intermediate 39 (1.5 g, 6.24 mmol) and gave in a 59% yield the title compound (1.6 g, 3 mmol).
$^1$H NMR (CDCl$_3$, 300 Mhz) δ: 1.02 (t, 3H), 1.20 (t, 3H), 1.49 (s, 6H), 1.88 (m, 1H), 2.11 (m, 1H), 2.14 (s, 3H), 2.42 (s, 3H), 4.16 (q, 2H), 5 16 (t, 1H), 6.51 (dd, 1H), 6.56 (d, 1H), 6.67 (d, 1H), 7.62(d, 2H), 7.96 (d, 2H),

EXAMPLE 31

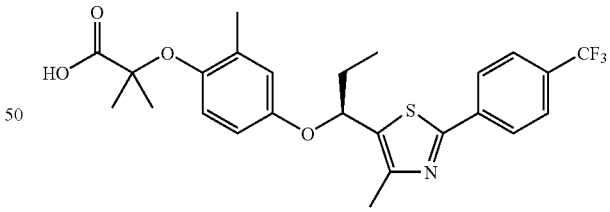

(S)-2-methyl-2-(2-methyl-4-{1-[4-methyl-2-(4-trifluoromethyl-phenyl)-thiazol-5-yl]propoxy}-phenoxy)-propionic acid The same saponification conditions as described for racemic example 3 were applied to example 30 (1.6 g, 3 mmol) and gave in a 74% yield the title compound as a viscous oil (1.1 g, 2.2 mmol) with an e.e.=83%.
$^1$H NMR(CDCl$_3$) δ: 1.03 (t, 3H), 1.51 (s, 6H), 1.89 (m, 1H), 2.12 (m, 1H), 2.16 (s, 3H), 2.24 (s, 3H), 5.18 (t, 1H), 6.55 (dd, 1H), 6.71 (m, 2H), 7.60 (d, 2H), 7.93 (d, 2H)
$[\alpha]^{25}_D$=−129 (c=0.322, CHCl$_3$) for e.e.=83%
HPLC: Chiralpak-AD (4.6×250 mm, 95% Hexane/5% EtOH ) Rt: 7.57 min

EXAMPLE 32

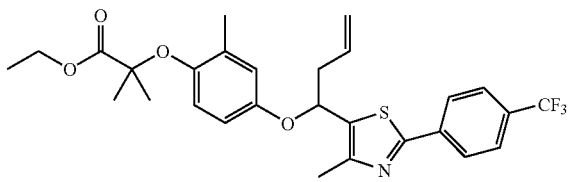

2-methyl-2-(2-methyl-4-{1-[4-methyl-2-(4-trifluoromethylphenyl)-thiazol-5-yl]but-3-enyloxy}phenoxy)pronionic acid ethyl ester To a solution of intermediate 39 (1.5 g, 6.3 mmol) and intermediate 32 (1.97 g, 6.3 mmol, 1 eq) in dry toluene was added PBu$_3$ (2.35 mL, 9.45 mmol, 1.5 eq). The resulting mixture was stirred at 0° C., and then TMAD (1.63 g, 9.45 mmol, 1.5 eq) was added. The mixture was stirred at 0° C. for 1 hour, and at RT for 24 hours. The resulting mixture was filtered off and concentrated in vacuo, and the title compound was obtained by flash chromatography using cyclohexane/ethyl acetate (8/2) as eluent, as a yellow oil (2.08 g, 3.9 mmol) in a 62% yield.

$^1$H NMR (CDCl$_3$): δ 1.21 (t, 3H), 15 (s, 6H), 2.15 (s, 3H), 2.42 (s, 3H), 2.65 (m, 1H), 2.85 (m, 1H), 4.2 (q, 2H), 5.15 (m, 2H), 5.30 (t, 1H), 5.85 (m, 1H), 6.55 (m, 2H), 6.7 (d, 1H), 7.65 (d, 2H), 7.97 (d, 2H),

LC/MS: C$_{28}$H$_{31}$F$_3$NO$_4$S: m/z 534.21 (M+1)

EXAMPLE 33

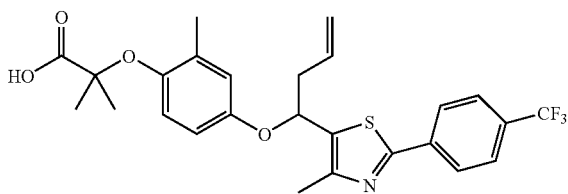

2-methyl-2-(2-methyl-4-{1-[4-methyl-2-(4-trifluoromethylphenyl)-thiazol-5-yl]but-3-enyloxy}phenoxy)propionic acid To a solution of example 32 (1 g, 1.87 mmol) in THF/ethanol (1/1) was added dropwise 0.2N NaOH (5.6 mmol, 3 eq). The resulting mixture was stirred at 50° C. for 3 hours, and after cooling at 0° C. 0.2N HCl (5.6 mmol, 3 eq) was added. The resulting mixture was concentrated in vacuo, then the residue was taken up in water and extracted with ethyl acetate. The organic phase was evaporated off and the residue was purified by flash chromatography using CH$_2$Cl$_2$/MeOH (97/3) as eluent. The residue was vigorously treated with 0.2N NaOH for 1 hour and then 0.2N HCl was added dropwise to yield to the precipitation of a white solid. After filtration, the white solid was washed with a small quantity of heptane to give the title compound (100 mg, 0.2 mmol) in a 11% yield as a white powder.

LC/MS: C$_{26}$H$_{27}$F$_3$NO$_4$S: m/z 505.97 (M+1)/ C$_{26}$H$_{25}$F$_3$NO$_4$S: m/z 504.04 (M−1)

EXAMPLE 34

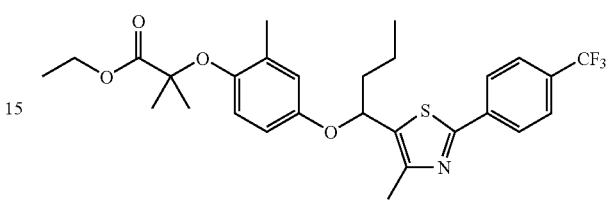

2-methyl-2-(2-methyl-4-{1-[4-methyl-2-(4-trifluoromethyl-phenyl)-thiazol-5-yl]butoxy}-phenoxy)-propionic acid ethyl ester A mixture of 1 g of example 32 (1.8 mmol), 100 mg of 10% Pd on charcoal in EtOH (50 mL) was stirred under an Hydrogen atmosphere at room temperature during 4 hours. The mixture was filtered through a celite pad and rinsed with 25 mL EtOH. The filtrate was concentrated to dryness to give the title compound (1.0 g, 2 mmol) as a brown powder in a quantitative crude yield.

MS: C$_{28}$H$_{33}$F$_3$NO$_4$S : m/z 536.1 (M+1)

EXAMPLE 35

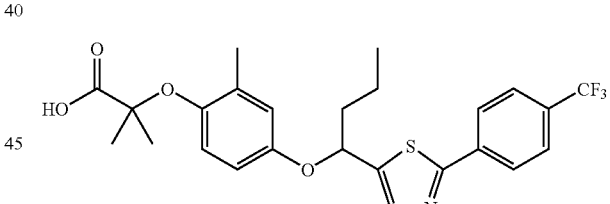

2-methyl-2-(2-methyl-4-{1-[4-methyl-2-(4-trifluoromethyl-phenyl)-thiazol-5-yl]butoxy}-phenoxy)-propionic acid To a solution of example 34 (800 mg, 1.5 mmol) in THF/Ethanol (5/20 mL) was added 1N NaOH (10 mmol, 10 mL). The resulting mixture was stirred at 50° C. for 2 hours, and after cooling at room temperature 1N HCl (10 mmol, 10 mL) was added. The resulting mixture was concentrated in vacuo, then the residue was flash chromatographed CH$_2$Cl$_2$/MeOH (98:2) to give the title compound (310 mg, 0.61 mmol) in a 40% yield as a colorless oil.

MS: C$_{26}$H$_{27}$F$_3$NO$_4$S: m/z 506.16 (M−1)
MS: C$_{26}$H$_{29}$F$_3$NO$_4$S: m/z 508.0 (M+1)

EXAMPLE 36

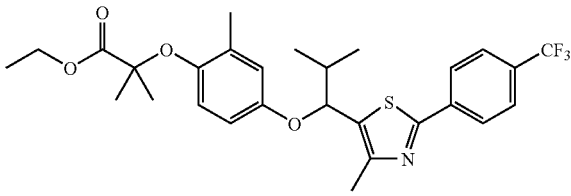

2-methyl-{2-methyl-2-(2-methyl-4-{1-[4-methyl-2-(4-trifluoromethyl-phenyl)-thiazol-5-yl]-propoxy}-phenoxy)}-propionic acid ethyl ester To a solution of phenol intermediate 39 (1.58 g, 6.6 mmol) and intermediate 31 (1.9 g, 6.6 mmol, 1.1 eq) in dry toluene was added PBu$_3$ (1.66 mL, 1.5 eq). The resulting mixture was allowed to warm to 0° C., and then TMAD (1.15 g, 1.5 eq) was added. The mixture was stirred at 0° C. for 1 hour, and at room temperature for 24 hours. The resulting mixture was filtered off and concentrated in vacuo, and the title compound was obtained by flash chromatography using Cyclohexane/Ethyl acetate (95/5), as a yellow oil (450 mg, 0.84 mmol) in a 14% yield.

MS: $C_{28}H_{33}F_3NO_4S$: m/z 536.1 (M+1)

EXAMPLE 37

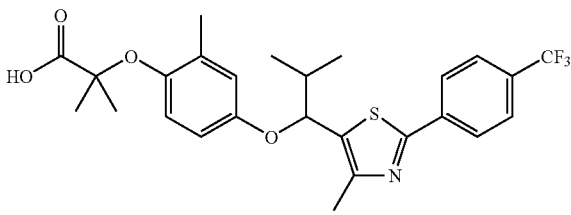

2-methyl-{2-methyl-2-(2-methyl-4-{1-[4-methyl-2-(4-trifluoromethyl-phenyl)-thiazol-5-yl]-propoxy}-phenoxy)}-propionic acid To a solution of example 36 (450 mg, 0.84 mmol) in THF/Ethanol (5/20 mL) was added 1N NaOH (5 mmol, 5 mL). The resulting mixture was stirred at 50° C. for 2 hours, and after cooling at room temperature 1N HCl (5 mmol, 5 mL) was added. The resulting mixture was concentrated in vacuo and the residue was flash chromatographed CH$_2$Cl$_2$/EtOAc (95:5) to give the title compound (290 mg, 0.57 mmol) in a 68% yield as an amorphous yellow powder.

MS: $C_{26}H_{27}F_3NO_4S$: m/z 506.24 (M−1)
MS: $C_{26}H_{29}F_3NO_4S$; m/z 508.1 (M+1)

EXAMPLE 38

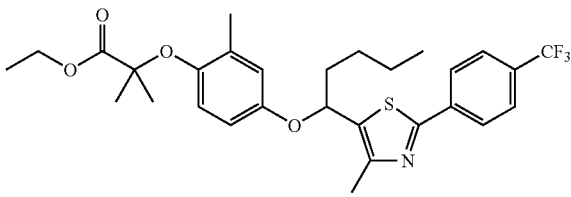

2-methyl-2-(2-methyl-4-{1-[4-methyl-2-(4-trifluoromethyl-phenyl)-thiazol-5-yl]pentyloxy}-phenoxy)-propionic acid ethyl ester To a solution of Intermediate 39 (238 mg, 1 mmol) and intermediate 33 (329 mg, 1 mmol, 1 eq) in dry toluene was added PBu$_3$ (1.5 mmol, 1.5 eq). The resulting mixture was allowed to warm to 0° C., and then TMAD (1.55 mmol, 1.5 eq) was added. The mixture was stirred at 0° C. for 1 hour, and at room temperature for 24 hours. The resulting mixture was filtered off and concentrated in vacuo, and the title compound was obtained by flash chromatography using Cyclohexane/EtOAc (90:10), as a yellow oil (100 mg, 0.18 mmol) in a 18% yield.

$^1$H NMR(CDCl$_3$) δ: 0.8 (t, 3H), 1.15 (t, 3H), 1.25 (m, 2H), 1.4 (s, 6H), 1.75 (m, 1H), 2.05 (m, 4H), 2.3 (s, 3H), 4.1 (q, 2H), 5.15 (t, 1H), 6.45 (dd, 1H), 6.55 (d, 1H), 6.6 (d, 1H), 7.55 (d, 2H), 7.9 (d, 2H)

EXAMPLE 39

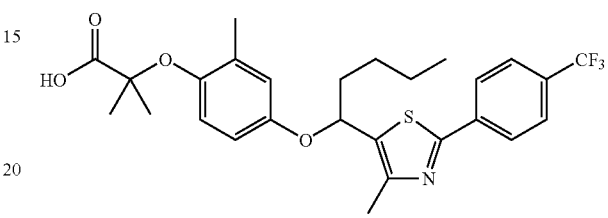

2-methyl-2-(2-methyl-4-{1-[4-methyl-2-(4-trifluoromethyl-phenyl)-thiazol-5-yl]pentyloxy}-phenoxy)-propionic acid To a solution of example 38 (90 mg, 0.164 mmol) in THF/Ethanol (1/1) was added 1N NaOH (5 mmol, 5 mL). The resulting mixture was stirred at 80° C. for 1.5 hour, and after cooling at room temperature 1N HCl (5 mmol, 5 mL) was added. The resulting mixture was concentrated in vacuo, then the residue was flash chromatographed eluting with CH$_2$Cl$_2$/EtOAc (90:10) to give the title compound (20 mg, 0.038 mmol) in a 23% yield as a colorless oil.

$^1$H NMR(CDCl$_3$) δ: 0.8 (t, 3H), 1.15-1.35 (m, 4H), 1.45 (s, 6H), 1.8 (m, 1H), 2.05 (m, 4H), 2.35 (s, 3H); 5.15 (t, 1H), 6.45 (m, 1H), 6.65 (m, 2H), 7.55 (d, 2H), 7.9 (d, 2H)

EXAMPLE 40

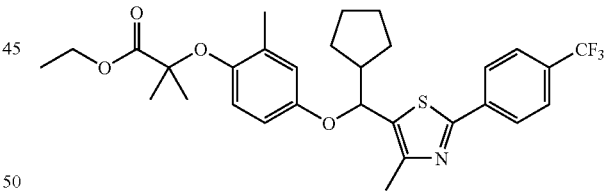

2-(4-{cyclopentyl-[4-methyl-2-(4-trifluoromethyl-phenyl)-thiazol-5-yl]-methoxy}-2-methyl-phenoxy)-2-methyl-propionic acid ethyl ester To a solution of Intermediate 39 (714 mg, 3 mmol) and intermediate 34 (1.024 g, 3 mmol, 1.1 eq) in dry toluene was added PBu$_3$ (1.1 mL, 1.5 eq). The resulting mixture was allowed to warm to 0° C., and then TMAD (774 mg, 1.5 eq) was added. The mixture was stirred at 0° C. for 1 hour, and at room temperature for 24 hours. The resulting mixture was filtered off and concentrated in vacuo, and the title compound was obtained as a viscous yellow oil (950 mg, 0.84 mmol) in a 56% yield by flash chromatography using Cyclohexane/EtOAc (95:5)

LC/MS : $C_{30}H_{35}F_3NO_4S$: m/z 562.0 (M+1)

EXAMPLE 41

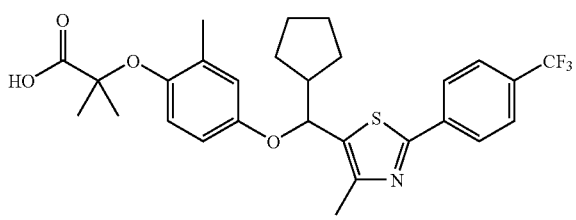

2-(4-{cyclopentyl-[4-methyl-2-(4-trifluoromethyl-phenyl)-thiazol-5-yl]-methoxy}-2-methyl-phenoxy)-2-methyl-propionic acid To a solution of example 40 (930 mg, 1.66 mmol) in THF/Ethanol (10/60 mL) was added dropwise 1N NaOH (8.3 mmol, 8.3 mL) diluted in 15 mL of water. The resulting mixture was stirred at 60° C. for 4 hours, and after cooling at room temperature 1N HCl (9 mmol, 9 mL) diluted in 20 mL of water was added. The resulting mixture was concentrated in vacuo and the residue was flash chromatographed $CH_2Cl_2$/MeOH (98:2) to give the title compound (690 mg, 1.29 mmol) in a 78% yield as a white amorphous powder.

LC/MS: $C_{28}H_{29}F_3NO_4S$: m/z 532.2 (M−1)

LC/MS: $C_{28}H_{31}F_3NO_4S$: m/z 534.2 (M+1)

EXAMPLE 42

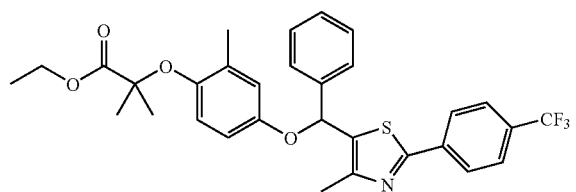

2-methyl-2-(2-methyl-4-{1-[4-methyl-2-(4-trifluoromethylphenyl)-thiazol-5-yl]phenylmethoxy}phenoxy)propionic acid ethyl ester To a solution of intermediate 39 (715 mg, 3 mmol) and intermediate 35 (1.05 g, 3 mmol, 1 eq) in dry toluene was added PBu$_3$ (1.11 mL, 4.5 mmol, 1.5 eq). The resulting mixture was allowed to stir at 0° C., and then TMAD (775 mg, 4.5 mmol, 1.5 eq) was added. The mixture was stirred at 0° C. for 1 hour, and at room temperature for 24 hours. The resulting mixture was filtered off and concentrated in vacuo, and the title compound was obtained by flash chromatography using cyclohexane/ethyl acetate (85:15) as eluent, as a yellow oil (870 mg, 1.53 mmol) in a 51% yield.

LC/MS: $C_{31}H_{31}F_3NO_4S$: m/z 569.99 (M+1)

EXAMPLE 43

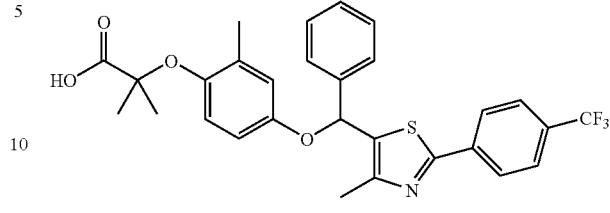

2-methyl-2-(2-methyl-4-{1-[4-methyl-2-(4-trifluoromethylphenyl)-thiazol-5-ylphenylmethoxy}phenoxy)propionic acid To a solution of example 42 (740 mg, 1.3 mmol) in THF/ethanol (1/1) was added dropwise 0.2N NaOH (6.5 mmol, 5 eq). The resulting mixture was stirred at 50° C. for 4 hours, and after cooling at 0° C. 0.2N HCl (6.5 mmol, 5 eq) was added. The resulting mixture was concentrated in vacuo, then the residue was taken up in water and extracted with ethyl acetate. The organic phase was evaporated off and the residue was purified by flash chromatography using $CH_2Cl_2$/ethyl acetate (80/20) as eluent. The residue was vigorously treated with 0.2N NaOH for 1 hour and then 0.2N HCl was added dropwise to yield to the precipitation of a white solid. After filtration, the white solid was washed with a small quantity of heptane to give the title compound (300 mg, 0.55 mmol) in a 43% yield.

LC/MS: $C_{29}H_{27}F_3NO_4S$: m/z 541.94 (M+1)/$C_{29}H_{25}F_3NO_4S$: m/z 540.03 (M−1)

EXAMPLE 44

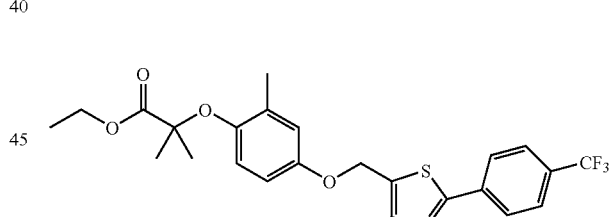

2-methyl-2-(2-methyl-4-[4-methyl-2-(4-trifluoromethylphenyl)thiazol-5-yl-methoxy]phenoxy)propionic acid ethyl ester 480 mg of Intermediate 39 (2 mmol) in 50 mL of acetone were stirred with 1 g of $Cs_2CO_3$ for 15 minutes. Intermediate 40 (651 mg, 2.2 mmol) was added and the mixture heated to reflux for 1 hour. After filtration and concentration under vacuo the residue was taken up with 200 mL of $CH_2Cl_2$ and washed with water. The organic layer was dried over $Na_2SO_4$, filtered and concentrated to afford 0.9 g of the expected compound as an oil.

$^1$H NMR (CDCl$_3$): δ 1.21 (t, 3H), 1.5 (s, 6H), 2.17 (s, 3H), 2.42 (s, 3H), 4.2 (q, 2H), 5.05 (s, 2H), 6.62 (dd, 1H), 6.75 (m, 2H), 7.58 (d, 2H), 7.92 (d, 2H),

EXAMPLE 45

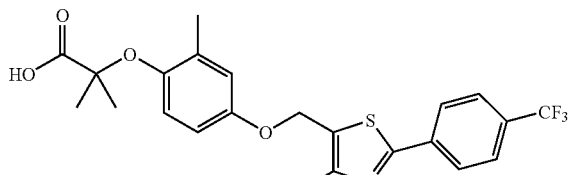

2-methyl-2-(2-methyl-4-[4-methyl-2-(4-trifluoromethylphenyl)thiazol-5-yl-methoxy]phenoxy)propionic acid 900 mg of example 44 dissolved in 30 mL of EtOH and 10 mL of 1N NaOH were heated to reflux for 1 hour. After cooling to room temperature the solution was acidified with 1N HCl and concentrated under vacuo. Trituration of the residue with water afforded after filtration and washing with water an off white powder which was recrystallized with $CH_3CN$ to give 370 mg of the title compound as slightly yellow crystals.

mp: 154° C.

EXAMPLE 46

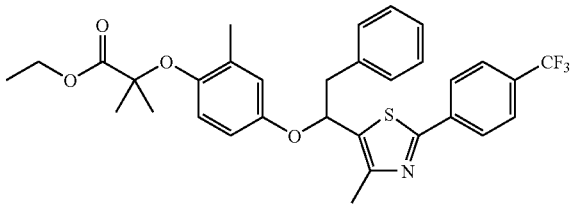

2-methyl-2-(2-methyl-4-{1-[4-methyl-2-(4-trifluoromethyl-phenyl)-thiazol-5-yl]-2-phenyl-ethoxy}-phenoxy)-propionic acid ethyl ester The same Mitsunobu conditions as described for racemic example 2 were applied to Intermediate 36 (1 g, 2.75 mmol) and phenol Intermediate 39 (655 mg, 2.75 mmol) and afforded in a 21% yield the title compound (340 mg, 0.58 mmol) as a brown residue after purification by flash chromatography $C_6H_{12}$/EtOAc (9:1).

LC/MS $C_{32}H_{33}F_3NO_4S$ m/z 584.2 (M+1)

EXAMPLE 47

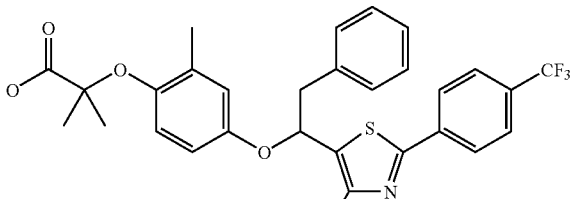

2-methyl-2-(2-methyl-4-{1-[4-methyl-2-(4-trifluoromethyl-phenyl)-thiazol-5-yl]-2-phenyl-ethoxy}-phenoxy)-propionic acid The same saponification conditions as described for racemic example 3 were applied to example 46 (280 mg, 0.48 mmol) and gave in a 79% yield the title compound (210 mg, 0.37 mmol) after flash chromatography $CH_2Cl_2$/MeOH (95: 5) as an amorphous brown powder.

LC/MS $C_{30}H_{27}F_3NO_4S$ m/z 554.3 (M−1)

EXAMPLE 48

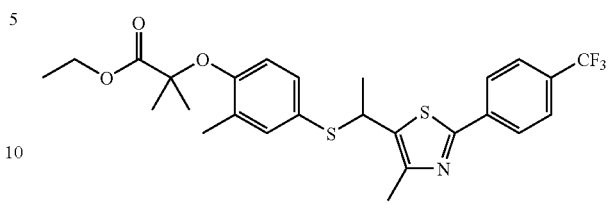

2-methyl-2-(2-methyl-4-{1-[4-methyl-2-(4-trifluoromethyl-phenyl)-thiazol-5-yl]-ethylsulfanyl}-phenoxy)-propionic acid ethyl ester To a suspension of intermediate 16 (287 mg, 1 mmol) and $ZnI_2$ (160 mg, 0.5 mmol) in 10 mL $CH_2Cl_2$ was added intermediate thiophenol 44 (305 mg, 1.2 mmol) in solution in 10 mL of $CH_2Cl_2$. After stirring 24 hours at rt the reaction was not complete and a supplementary equivalent of $ZnI_2$ (319 mg, 1 mmol) was added. The mixture was stirred 24 hours at rt quenched with water (10 mL) and 100 mL of $CH_2Cl_2$ were added and the organic phase separated dried over $Na_2SO_4$ concentrated under vacuo and purified by flash chromatography $C_6H_{12}$/EtOAc (90:10). The title compound (320 mg, 0.61 mmol) was obtained as a colorless viscous oil in a 61% yield.

LC/MS: $C_{26}H_{29}F_3NO_3S_2$ m/z 523.98 (M+1)

EXAMPLE 49

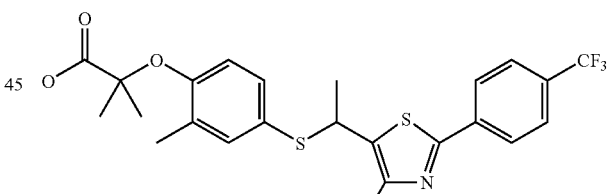

2-methyl-2-(2-methyl-4-{1-[4-methyl-2-(4-trifluoromethyl-phenyl)-thiazol-5-yl]-ethylsulfanyl}-phenoxy)-propionic acid The same saponification conditions as described for racemic example 3 were applied to example 48 (290 mg, 0.56 mmol) and gave in a 47% yield the title compound as a white powder (130 mg, 0.262 mmol).

$^1$H NMR ($CDCl_3$) δ: 1.59 (s, 6H), 1.68 (d, 3H), 1.99 (s, 3H), 2.14 (s, 3H), 4.41 (q, 1H), 6.61 (dd, 1H), 6.95 (dd, 1H), 7.04 (brs, 1H), 7.15 (d, 1H), 7.66 (d, 2H), 7.94 (d, 2H)

EXAMPLE 50

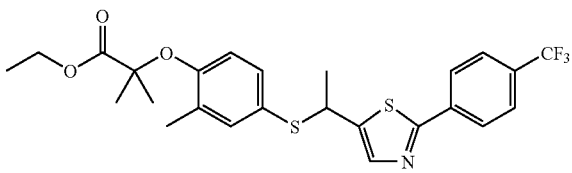

2-methyl-2-(2-methyl-4-{1-[2-(4-trifluoromethyl-phenyl)-thiazol-5-yl]-ethylsulfanyl]-phenoxy)-propionic acid ethyl ester The same Mitsunobu conditions as described for racemic example 2 were applied to Intermediate 17 (350 mg, 1.3 mmol) and thiophenol Intermediate 44 (358 mg, 1.3 mmol) and afforded in a 80% yield the title compound (520 mg, 1.02 mmol) as an oil after purification by flash chromatography $CH_2Cl_2$
$^1H$ NMR ($CDCl_3$) δ: 1.24 (t, 3H), 1.62 (s, 6H), 1.74 (d, 3H), 2.20 (s, 3H), 4.24 (q, 2H), 4.50 (q, 1H), 6.56 (d, 1H), 7.07 (dd, 1H), 7.20 (d, 1H), 7.71 (d, 2H), 8.03 (d, 2H)

EXAMPLE 51

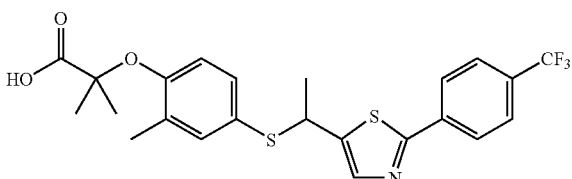

2-methyl-2-(2-methyl-4-{1-[2-(4-trifluoromethyl-phenyl)-thiazol-5-yl]-ethylsulfanyl}-phenoxy)-propionic acid The same saponification conditions as described for racemic example 3 were applied to example 50 (520 mg, 1.02 mmol) and gave in a quantitative yield the title compound as an off-white powder.
LC/MS $C_{23}H_{23}F_3NO_3S_2$ m/z 481.93 (M+1)
LC/MS $C_{23}H_{21}F_3NO_3S_2$ m/z 480.00 (M−1)

EXAMPLE 52

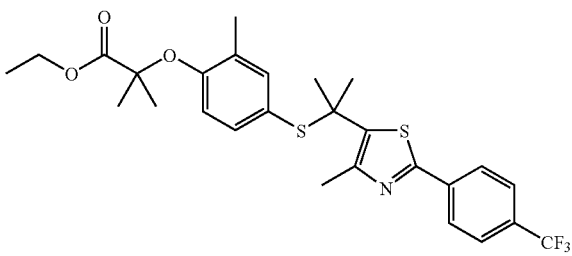

2-methyl-2-(2-methyl-4-{1-methyl-1-[4-methyl-2-(4-trifluoromethyl-phenyl)-thiazol-5-yl]-ethylsulfanyl}-phenoxy)-propionic acid ethyl ester The same coupling conditions as described for example 48 were applied to Intermediate 24 (350 mg, 1.16 mmol) and thiophenol intermediate 44 (354 mg, 1.3 mmol) and afforded in a 22% yield the title compound (140 mg, 0.26 mmol) as a colorless oil after purification by flash chromatography C6H12/EtOAc (80:20)
LC/MS $C_{27}H_{31}F_3NO_3S_2$ m/z 538 (M+1)

EXAMPLE 53

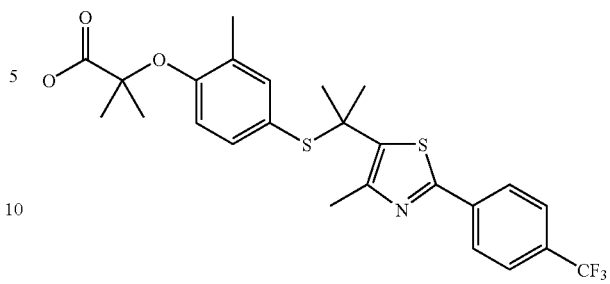

2-methyl-2-(2-methyl-4-{1-methyl-1-[4-methyl-2-(4-trifluoromethyl-phenyl)-thiazol-5-yl]-ethylsulfanyl}-phenoxy)-propionic acid The same saponification conditions as described for racemic example 3 were applied to example 52 (140 mg, 0.26 mmol) and gave in a 52% yield the title compound (70 mg, 0.13 mmol) as a colorless oil.
LC/MS $C_{25}H_{27}F_3NO_3S_2$ m/z 510.1 (M+1)
LC/MS $C_{25}H_{25}F_3NO_3S_2$ m/z 508.2 (M−1)

EXAMPLE 54

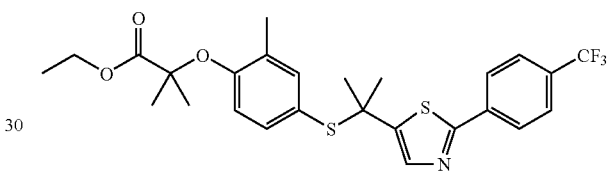

2-methyl-2-(2-methyl-4-{1-methyl-1-[2-(4-trifluoromethyl-phenyl)-thiazol-5-yl]-ethylsulfanyl}-phenoxy)-propionic acid ethyl ester The same coupling conditions as described for example 48 were applied to Intermediate 25 (350 mg, 1.22 mmol) and thiophenol intermediate 44 (371 mg, 1.4 mmol) and afforded in a 46% yield the title compound (300 mg, 0.57 mmol) as a colorless oil after purification by flash chromatography $CH_2Cl_2$.
$^1H$ NMR ($CDCl_3$) δ: 1.1 (t, 3H), 1.46 (s, 6H), 1.63 (s, 6H), 2.05 (s, 3H), 4.1 (q, 2H), 6.4 (d, 1H), 6.85 (dd, 1H), 6.98 (d, 1H), 7.62 (d, 2H), 7.95 (d, 2H)

EXAMPLE 55

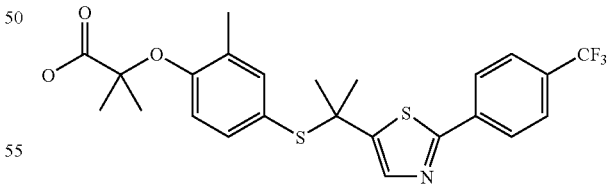

2-methyl-2-(2-methyl-4-{1-methyl-1-[2-(4-trifluoromethyl-phenyl)-thiazol-5-yl]-ethylsulfanyl}-phenoxy)-propionic acid The same saponification conditions as described for racemic example 3 were applied to example 54 (300 mg, 0.54 mmol) and gave in a 48% yield the title compound (130 mg, 0.262 mmol) as a gummy solid.
LC/MS $C_{24}H_{25}F_3NO_3S_2$ m/z 496.0 (M+1)

EXAMPLE 56

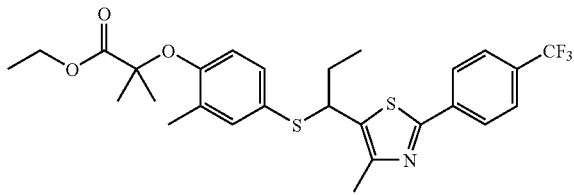

2-methyl-2-(2-methyl-4-{1-[4-methyl-2-(4-trifluoromethyl-phenyl)-thiazol-5-yl]-propylsulfanyl}-phenoxy)-propionic acid ethyl ester The same coupling conditions as described for example 48 were applied to Intermediate 26 (800 mg, 2.6 mmol) and thiophenol intermediate 44 (660 mg, 2.6 mmol) and afforded in a 71% yield the title compound (1000 mg, 1.86 mmol) as a slightly yellow oil after purification by flash chromatography $C_6H_{12}$/EtOAc (95:5).

LC/MS $C_{27}H_{31}F_3NO_3S_2$ m/z 538.01 (M+1)

EXAMPLE 57

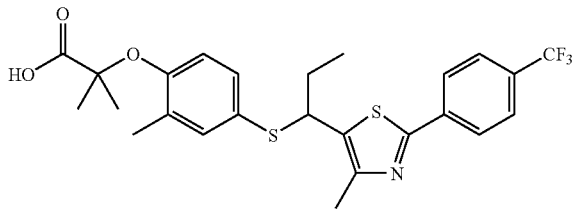

2-methyl-2-(2-methyl-4-{1-[4-methyl-2-(4-trifluoromethyl-phenyl)-thiazol-5-yl]-propylsulfanyl}-phenoxy)-propionic acid The same saponification conditions as described for racemic example 3 were applied to example 56 (1 g, 1.86 mmol) and gave in a 88% yield the title compound (840 mg, 1.65 mmol) as an amorphous white powder.

LC/MS $C_{25}H_{27}F_3NO_3S_2$ m/z 510.0 (M+1)
LC/MS $C_{25}H_{25}F_3NO_3S_2$ m/z 508.1 (M−1)

The following intermediates and ligands were prepared for the binding and transfection assays described below:

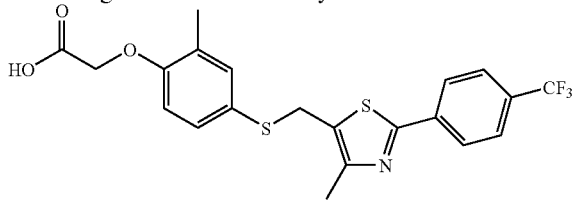

(i) 2-{2-methyl-4-[({4-methyl-2-[4-(trifluoromethyl)phenyl]-1,3-thiazol-5-yl}methyl)sulfanyl]phenoxy}acetic acid This compound was used as a PPARdelta reference in the transfection assays described below and was prepared according to the method reported in WO200100603-A1

(ii) 2-methyl-2-[4-{[(4-methyl-2-[4-trifluoromethylphenyl]-thiazol-5-yl carbonyl)amino]methyl}-phenoxy]propionic acid This compound was used as a PPAR alpha reference in the transfection assay described below and was prepared according to method reported in WO200140207-A1

(iii) 5-{4-[2-(Methyl-pyridin-2-yl-amino)-ethoxy]-benzyl}-thiazolidine-2,4-dione This compound was used as a PPAR gamma reference in the transfection assay described below and was prepared according to method reported in J. Med. Chem. 1994, 37(23), 3977

Binding Assay:

Compounds were tested for their ability to bind to hPPAR gamma hPPARalpha or PPARdelta using a Scintillation Proximity Assay (SPA). The PPAR ligand binding domain (LBD) was expressed in E. coli as polyHis tagged fusion proteins and purified. The LBD was then labelled with biotin and immobilised on streptavidin-modified scintillation proximity beads. The beads were then incubated with a constant amount of the appropriate radioligand (3H-BRL 49653 for PPAR-gamma, radiolabelled 2-(4-(2-(2,3-Ditritio-1-heptyl-3-(2,4-difluorophenyl)ureido)ethyl)phenoxy)-2-methylbutanoic acid for hPPAR alpha (see WO 00/08002) and labelled GW 2433 (see Brown, P. J et al. Chem. Biol., 4, 909-918 (1997). For the structure and synthesis of this ligand) for PPAR delta) and variable concentrations of test compound, and after equilibration the radioactivity bound to the beads was measured by a scintillation counter. The amount of nonspecific binding, as assessed by control wells containing 50 µM of the corresponding unlabeled ligand, was subtracted from each data point. For each compound tested, plots of ligand concentration vs. CPM of radioligand bound were constructed and apparent KI values were estimated from nonlinear least squares fit of the data assuming simple competitive binding. The details of this assay have been reported elsewhere (see, Blanchard, S. G. et. al. Development of a Scintillation Proximity Assay for Peroxisome Proliferator-Activated Receptor gamma Ligand Binding Domain. Anal. Biochem., 257, 112-119 (1998)).

Transfection Assay:

Compounds were screened for functional potency in transient transfection assays in CV-1 cells for their ability to activate the PPAR subtypes (transactivation assay). A previously established chimeric receptor system was utilized to allow comparison of the relative transcriptional activity of the receptor subtypes on the same target gene and to prevent endogenous receptor activation from complicating the interpretation of results. See, for example, Lehmann, J. M., Moore, L. B.; Smith-Oliver, T. A.; Wilkison, W. O.; Willson, T. M.; Kliewer, S. A., An antidiabetic thiazolidinedione is a high affinity ligand for peroxisome proliferator-activated receptor gamma (PPARgamma), J. Biol. Chem., 270, 12953-6 (1995). The ligand binding domains for murine and human PPAR alpha, PPAR gamma, and PPAR delta were each fused to the yeast transcription factor GAL4 DNA binding domain. CV-1 cells were transiently transfected with expression vectors for the respective PPAR chimera along with a reporter construct containing five copies of the GAL4 DNA binding site driving expression of secreted placental alkaline phosphatase (SPAP) and beta-galactosidase. After 16 h, the medium was exchanged to DME medium supplemented with 10% delipidated fetal calf serum and the test compound at the appropriate concentration. After an additional 24 h, cell extracts were prepared and assayed for alkaline phosphatase and β-galactosidase activity. Alkaline phosphatase activity was corrected for transfection efficiency using the beta-galactosidase activity as an internal standard (see, for example, Kliewer, S. A., et. al. Cell 83, 813-819 (1995)). Rosiglitazone (BRL 49653) was used as a positive control in the hPPAR gamma assay. The positive control in the hPPAR alpha assays was 2-methyl-2-[4-{[(4-methyl-2-[4-trifluoromethylphenyl]-thiazol-5-yl-carbonyl)amino]methyl}-phenoxy]propionic acid. The positive control for PPAR delta assays was 2-{2-methyl-4-[({4-methyl-2-{trifluoromethyl)phenyl]-1,3-thiazol-5-yl}methyl)sulfanyl] phenoxy}acetic acid.

All of the above acid Examples showed at least 50% activation of hPPARδ relative to the positive control at concentrations of $10^{-7}$ M or less.

Activities in three hPPAR subtypes are reported in the table below for the most preferred compounds and are expressed in nanomolar.

| Example | EC50 hPPAR α | EC50 hPPAR δ | EC50 hPPAR γ |
|---------|--------------|--------------|--------------|
| 1       | 43           | 2.5          | 57           |
| 9       | 16           | 3            | 7000         |
| 11      | 10           | 0.7          | 300          |
| 31      | 5            | 1.7          | 660          |
| 29      | 9            | 1.5          | 240          |

What is claimed is:

1. A method of treating a hPPAR mediated disease or condition in a patient wherein the hPPAR mediated disease or condition is selected from the group consisting of dyslipidemia, syndrome X, heart failure, hypercholesteremia, type II diabetes mellitus, type I diabetes, insulin resistance, hyperlipidemia, obesity, anorexia bulimia and anorexia nervosa comprising the administration of:

(a) a compound of formula (I) or a pharmaceutically acceptable salt, or hydrolysable ester thereof,

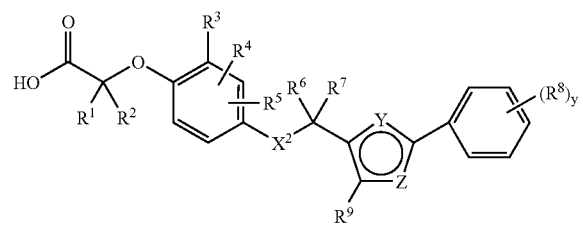

(1)

wherein:

$R^1$ and $R^2$ are independently H or $C_{1-3}$ alkyl, or $R^1$ and $R^2$ which are bonded to the same carbon atom may together with the carbon atom to which they are bonded form a 3-6 membered cycloalkyl ring, and at least one of $R^1$ and $R^2$ must be other than H;

$X^2$ is O or S;

$R^3$, $R^4$, and $R^5$ are independently H, $C_{1-3}$alkyl, $OCH_3$, $CF_3$, allyl, or halogen;

one of Y and Z is N, the other is S or O;

$R^6$ and $R^7$ are independently H, phenyl, benzyl, fluorine OH, $C_{1-6}$ alkyl, or allyl, or $R^6$ and $R^7$ may, together with the carbon atom to which they are bonded, represent a carbonyl group;

$R^9$ is H, $CF_3$ or $CH_3$;

each $R^8$ is independently $CF_3$, $C_{1-3}$alkyl, $OCH_3$ or halogen; and y is 1 or 2; and (b) a statin.

2. A method of treating a hPPAR mediated disease or condition in a patient wherein the hPPAR mediated disease or condition is selected from the group consisting of dyslipidemia, syndrome X, heart failure, hypercholesteremia, type II diabetes mellitus, type I diabetes, insulin resistance, hyperlipidemia, obesity, anorexia bulimia and anorexia nervosa comprising the administration of:

(a) a compound of formula (I) or a pharmaceutically acceptable salt, or hydrolysable ester thereof,

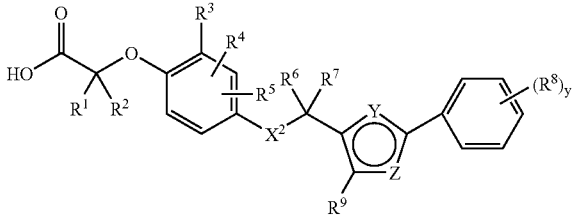

(1)

wherein:

$R^1$ and $R^2$ are independently H or $C_{1-3}$ alkyl, or $R^1$ and $R^2$ which are bonded to the same carbon atom may together with the carbon atom to which they are bonded form a 3-6 membered cycloalkyl ring, and at least one of $R^1$ and $R^2$ must be other than H;

$X^2$ is O or S;

$R^3$, $R^4$, and $R^5$ are independently H, $C_{1-3}$alkyl, $OCH_3$, $CF_3$, allyl, or halogen;

one of Y and Z is N, the other is S or O;

$R^6$ and $R^7$ are independently H, phenyl, benzyl, fluorine OH, $C_{1-6}$ alkyl, or allyl, or $R^6$ and $R^7$ may, together with the carbon atom to which they are bonded, represent a carbonyl group;

$R^9$ is H, $CF_3$ or $CH_3$;

each $R^8$ is independently $CF_3$, $C_{1-3}$alkyl, $OCH_3$ or halogen; and y is 1 or 2; and (b) at least one additional antidiabetic agent.

3. A method of treating a hPPAR mediated disease or condition in a patient wherein the hPPAR mediated disease or condition is selected from the group consisting of dyslipidemia, syndrome X, heart failure, hypercholesteremia, type II diabetes mellitus, type I diabetes, insulin resistance, hyperlipidemia, obesity, anorexia bulimia and anorexia nervosa comprising the administration of:

(a) a compound of formula (I) or a pharmaceutically acceptable salt, or hydrolysable ester thereof,

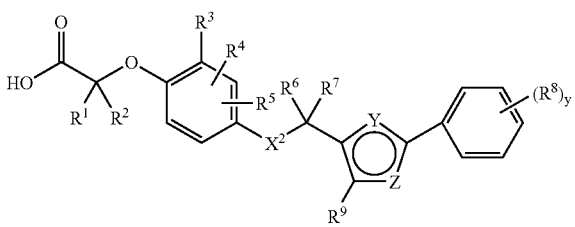

(1)

wherein:

$R^1$ and $R^2$ are independently H or $C_{1-3}$ alkyl, or $R^1$ and $R^2$ which are bonded to the same carbon atom may together with the carbon atom to which they are bonded form a 3-6 membered cycloalkyl ring, and at least one of $R^1$ and $R^2$ must be other than H;

$X^2$ is O or S;

$R^3$, $R^4$, and $R^5$ are independently H, $C_{1-3}$alkyl, $OCH_3$, $CF_3$, allyl, or halogen;

one of Y and Z is N, the other is S or O;

$R^6$ and $R^7$ are independently H, phenyl, benzyl, fluorine OH, $C_{1-6}$ alkyl, or allyl, or $R^6$ and $R^7$ may, together with the carbon atom to which they are bonded, represent a carbonyl group;

$R^9$ is H, $CF_3$ or $CH_3$;

each $R^8$ is independently $CF_3$, $C_{1-3}$alkyl, $OCH_3$ or halogen; and y is 1 or 2; and (b) an antihypertensive agent.

4. A pharmaceutical composition comprising:

(a) a compound of formula (I) or a pharmaceutically acceptable salt, or hydrolysable ester thereof,

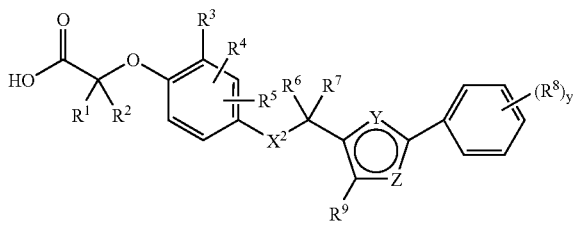

(1)

wherein:

$R^1$ and $R^2$ are independently H or $C_{1-3}$ alkyl, or $R^1$ and $R^2$ which are bonded to the same carbon atom may together with the carbon atom to which they are bonded form a 3-6 membered cycloalkyl ring, and at least one of $R^1$ and $R^2$ must be other than H;

$X^2$ is O or S;

$R^3$, $R^4$, and $R^5$ are independently H, $C_{1-3}$alkyl, $OCH_3$, $CF_3$, allyl, or halogen;

one of Y and Z is N, the other is S or O;

$R^6$ and $R^7$ are independently H, phenyl, benzyl, fluorine OH, $C_{1-6}$ alkyl, or allyl, or $R^6$ and $R^7$ may, together with the carbon atom to which they are bonded, represent a carbonyl group;

$R^9$ is H, $CF_3$ or $CH_3$;

each $R^8$ is independently $CF_3$, $C_{1-3}$alkyl, $OCH_3$ or halogen; and y is 1 or 2; and (b) a statin.

5. A pharmaceutical composition comprising:

(a) a compound of formula (I) or a pharmaceutically acceptable salt, or hydrolysable ester thereof,

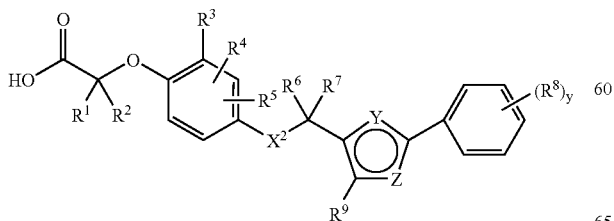

(1)

wherein:

$R^1$ and $R^2$ are independently H or $C_{1-3}$ alkyl, or $R^1$ and $R^2$ which are bonded to the same carbon atom may together with the carbon atom to which they are bonded form a 3-6 membered cycloalkyl ring, and at least one of $R^1$ and $R^2$ must be other than H;

$X^2$ is O or S;

$R^3$, $R^4$, and $R^5$ are independently H, $C_{1-3}$alkyl, $OCH_3$, $CF_3$, allyl, or halogen;

one of Y and Z is N, the other is S or O;

$R^6$ and $R^7$ are independently H, phenyl, benzyl, fluorine OH, $C_{1-6}$ alkyl, or allyl, or $R^6$ and $R^7$ may, together with the carbon atom to which they are bonded, represent a carbonyl group;

$R^9$ is H, $CF_3$ or $CH_3$;

each $R^8$ is independently $CF_3$, $C_{1-3}$alkyl, $OCH_3$ or halogen; and y is 1 or 2; and (b) at least one additional antidiabetic agent.

6. A pharmaceutical composition comprising:

(a) a compound of formula (I) or a pharmaceutically acceptable salt, or hydrolysable ester thereof,

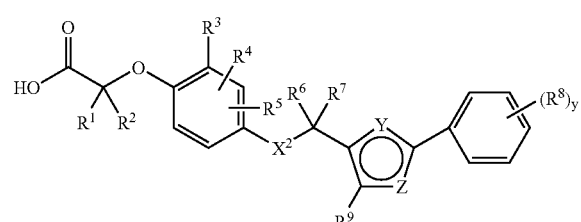

(1)

wherein:

$R^1$ and $R^2$ are independently H or $C_{1-3}$ alkyl, or $R^1$ and $R^2$ which are bonded to the same carbon atom may together with the carbon atom to which they are bonded form a 3-6 membered cycloalkyl ring, and at least one of $R^1$ and $R^2$ must be other than H;

$X^2$ is O or S;

$R^3$, $R^4$, and $R^5$ are independently H, $C_{1-3}$alkyl, $OCH_3$, $CF_3$, allyl, or halogen;

one of Y and Z is N, the other is S or O;

$R^6$ and $R^7$ are independently H, phenyl, benzyl, fluorine OH, $C_{1-6}$ alkyl, or allyl, or $R^6$ and $R^7$ may, together with the carbon atom to which they are bonded, represent a carbonyl group;

$R^9$ is H, $CF_3$ or $CH_3$;

each $R^8$ is independently $CF_3$, $C_{1-3}$alkyl, $OCH_3$ or halogen; and y is 1 or 2; and (b) an antihypertensive agent.

7. A method of treating a hPPAR mediated disease or condition in a patient wherein the hPPAR mediated disease or condition is selected from the group consisting of dyslipidemia, syndrome X, heart failure, hypercholesteremia, type II diabetes mellitus, type I diabetes, insulin resistance, hyperlipidemia, obesity, anorexia bulimia and anorexia nervosa comprising the administration of:

(a) A compound of the formula

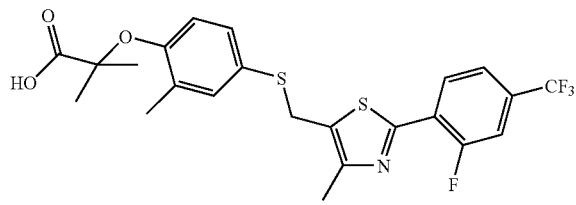

or a pharmaceutically acceptable salt or thereof; and (b) a statin.

8. A method of treating a hPPAR mediated disease or condition in a patient wherein the hPPAR mediated disease or condition is selected from the group consisting of dyslipidemia, syndrome X, heart failure, hypercholesteremia, type II diabetes mellitus, type I diabetes, insulin resistance, hyperlipidemia, obesity, anorexia bulimia and anorexia nervosa comprising the administration of:

(a) A compound of the formula:

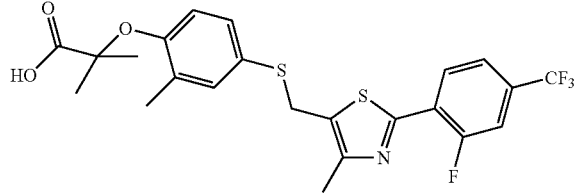

or a pharmaceutically acceptable salt or thereof; and (b) at least one additional antidiabetic agent.

9. A method of treating a hPPAR mediated disease or condition in a patient wherein the hPPAR mediated disease or condition is selected from the group consisting of dyslipidemia, syndrome X, heart failure, hypercholesteremia, type II diabetes mellitus, type I diabetes, insulin resistance, hyperlipidemia, obesity, anorexia bulimia and anorexia nervosa comprising the administration of:

(a) A compound of the formula:

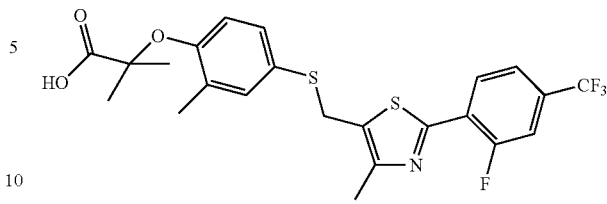

or a pharmaceutically acceptable salt or thereof; and
(b) an antihypertensive agent.

10. A pharmaceutical composition comprising:
(a) A compound of the formula:

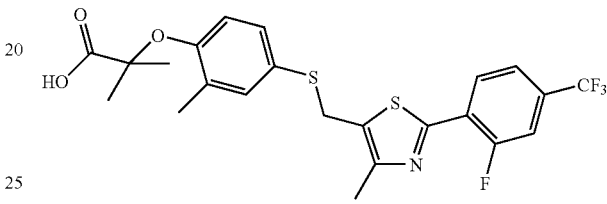

or a pharmaceutically acceptable salt thereof; and
(b) a statin.

11. A pharmaceutical composition comprising:
(a) A compound of the formula:

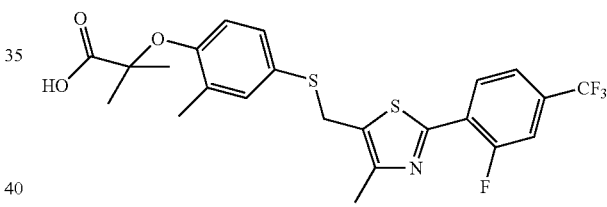

or a pharmaceutically acceptable salt thereof; and
(b) at least one additional antidiabetic agent.

12. A pharmaceutical composition comprising:
(a) A compound of the formula:

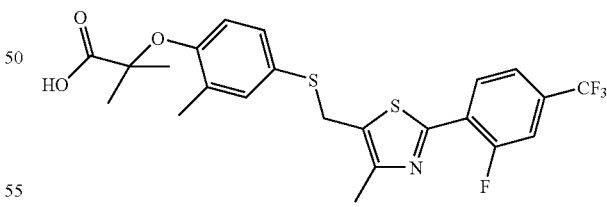

or a pharmaceutically acceptable salt thereof, and
(b) an antihypertensive agent.

* * * * *